US012376665B2

(12) United States Patent
Gouchtchina et al.

(10) Patent No.: US 12,376,665 B2
(45) Date of Patent: *Aug. 5, 2025

(54) DERMAL SPRAY APPARATUS WITH DISPOSABLE CARTRDIGE AND METHOD

(71) Applicant: Kozhya LLC Sp. z o.o., Poznań (PL)

(72) Inventors: Yoanna Gouchtchina, Allen, TX (US); Enrique Gallar, Berlin (DE)

(73) Assignee: Kozhya LLC SP. Z O.O., Poznan (PL)

( * ) Notice: Subject to any disclaimer, the term of this patent is extended or adjusted under 35 U.S.C. 154(b) by 641 days.

This patent is subject to a terminal disclaimer.

(21) Appl. No.: 17/501,831

(22) Filed: Oct. 14, 2021

(65) Prior Publication Data

US 2023/0123741 A1    Apr. 20, 2023

(51) Int. Cl.
| | |
|---|---|
| *A45D 34/04* | (2006.01) |
| *A45D 34/00* | (2006.01) |
| *A61M 11/02* | (2006.01) |
| *B05B 7/06* | (2006.01) |
| *B05B 7/24* | (2006.01) |
| *B05B 15/65* | (2018.01) |

(52) U.S. Cl.
CPC ........... *A45D 34/04* (2013.01); *A61M 11/02* (2013.01); *B05B 7/064* (2013.01); *B05B 7/066* (2013.01); *B05B 7/2408* (2013.01); *B05B 7/2435* (2013.01); *B05B 7/2443* (2013.01); *B05B 7/2481* (2013.01); *B05B 15/65* (2018.02); *A45D 2034/005* (2013.01); *A45D 2200/057* (2013.01); *A61M 2210/04* (2013.01)

(58) Field of Classification Search
CPC ....... B05B 7/064; B05B 7/066; B05B 7/2429; B05B 7/0869; B05B 7/2481; B05B 7/2435; B05B 7/2408; B05B 15/50; B05B 15/65; A45D 34/04; A61M 11/02
USPC .......................................... 239/272
See application file for complete search history.

(56) References Cited

U.S. PATENT DOCUMENTS

| | | | | |
|---|---|---|---|---|
| 2,078,171 | A | * | 4/1937 | Wittie ............... B05B 7/2437 239/371 |
| 2,802,448 | A | | 8/1957 | Young |
| D190,785 | S | | 6/1961 | Ralph |
| D191,650 | S | | 10/1961 | Kruck |
| D193,951 | S | | 10/1962 | Stephen |
| 3,554,450 | A | | 1/1971 | Muhala |
| D258,046 | S | | 1/1981 | Richmond |
| D308,162 | S | | 5/1990 | Nitta |

(Continued)

FOREIGN PATENT DOCUMENTS

| | | |
|---|---|---|
| CA | 43463 A | 4/1978 |
| CN | 2930731 | 8/2007 |

(Continued)

OTHER PUBLICATIONS

U.S. Appl. No. 29/837,786, filed May 9, 2022, Gouchtchina.

(Continued)

*Primary Examiner* — Cody J Lieuwen
(74) *Attorney, Agent, or Firm* — Jeff B. Vockrodt; CM Law

(57) ABSTRACT

A system and method for dermal spraying includes a portable, hand-held dermal application device with one or more disposable cartridges that spray a dermal formulation onto the skin, the disposable cartridge having a nozzle that can be activated by placing the cartridge into the spray device.

14 Claims, 27 Drawing Sheets

(56) References Cited

U.S. PATENT DOCUMENTS

| | | |
|---|---|---|
| D317,407 S | 6/1991 | Gray et al. |
| 5,248,096 A * | 9/1993 | Hoey .................. B05B 7/2481 |
| | | 604/296 |
| D356,828 S | 3/1995 | Harris |
| 5,613,272 A | 3/1997 | Huffman |
| 5,839,623 A | 11/1998 | Losenno et al. |
| D415,267 S | 10/1999 | Kauzlarich et al. |
| 6,125,844 A | 10/2000 | Samiotes |
| D450,889 S | 11/2001 | Chang |
| 6,326,062 B1 | 12/2001 | Noakes et al. |
| D463,736 S | 10/2002 | Hern |
| 6,478,193 B1 * | 11/2002 | Good .................. B05B 11/0029 |
| | | 215/220 |
| 6,598,808 B1 | 7/2003 | Garcia et al. |
| D526,717 S | 8/2006 | Yamaguchi et al. |
| D528,653 S | 9/2006 | Matthew |
| D529,811 S | 10/2006 | Ratzlaff |
| D530,621 S | 10/2006 | Rashid |
| D538,482 S | 3/2007 | Martinez |
| D541,169 S | 4/2007 | Ball |
| D543,455 S | 5/2007 | Winner |
| 7,225,807 B2 | 6/2007 | Papania et al. |
| D552,232 S | 10/2007 | Collins |
| D561,890 S | 2/2008 | Lithgow |
| D596,043 S | 7/2009 | Noble |
| 7,661,563 B2 | 2/2010 | De Lataulade |
| 7,874,461 B2 | 1/2011 | Bae |
| 7,959,597 B2 | 6/2011 | Baker et al. |
| 8,091,803 B2 | 1/2012 | Fedorov |
| D654,805 S | 2/2012 | Lua |
| D655,199 S | 3/2012 | Ciriani |
| 8,308,029 B2 | 11/2012 | Ki |
| D673,055 S | 12/2012 | Cappello |
| D673,264 S | 12/2012 | Kunze |
| 8,443,799 B2 | 5/2013 | Yamashita et al. |
| 8,584,971 B2 | 11/2013 | Seabase et al. |
| D698,208 S | 1/2014 | Cavanagh |
| D716,666 S | 11/2014 | Park |
| D733,565 S | 7/2015 | Leventhal |
| D734,153 S | 7/2015 | Fily |
| D751,415 S | 3/2016 | Otani |
| 9,358,561 B2 | 6/2016 | Johnson et al. |
| D764,309 S | 8/2016 | Yakos |
| D766,096 S | 9/2016 | Moreaux |
| D779,124 S | 2/2017 | Houyoux |
| D791,933 S | 7/2017 | Rabe |
| D796,025 S | 8/2017 | Lo |
| 9,744,319 B2 | 8/2017 | Denyer et al. |
| D811,893 S | 3/2018 | Bandawat |
| 10,099,233 B2 * | 10/2018 | Tsai .................... B05B 7/2489 |
| D833,079 S | 11/2018 | Fang |
| D834,702 S | 11/2018 | Evans |
| 10,252,283 B2 | 4/2019 | Gouchtchina et al. |
| D848,603 S | 5/2019 | Fujino |
| D849,230 S | 5/2019 | Gouchtchina |
| D855,891 S | 8/2019 | Lin |
| D871,134 S | 12/2019 | Silsby |
| D871,230 S | 12/2019 | Zhang |
| D889,635 S | 7/2020 | Mitchell et al. |
| D900,303 S | 10/2020 | Mitchell et al. |
| 10,814,077 B2 | 10/2020 | Dyche et al. |
| 10,835,691 B2 | 11/2020 | Dyche et al. |
| D905,846 S | 12/2020 | Mitchell et al. |
| D906,530 S | 12/2020 | Liu |
| D908,965 S | 1/2021 | Pae |
| D943,733 S | 2/2022 | Cavatorta |
| 11,273,267 B2 | 3/2022 | Gavini et al. |
| D958,672 S | 7/2022 | Warner |
| D962,070 S | 8/2022 | Yoshida |
| 11,439,218 B2 | 9/2022 | Gouchtchina et al. |
| D965,770 S | 10/2022 | Shah et al. |
| D970,352 S | 11/2022 | Chan |
| 11,641,921 B1 | 5/2023 | Gouchtchina et al. |
| D990,046 S | 6/2023 | Levy |
| 2003/0063801 A1 | 4/2003 | Rubinstenn et al. |
| 2003/0084914 A1 | 5/2003 | Simon |
| 2003/0157183 A1 | 8/2003 | Perrut |
| 2004/0050964 A1 | 3/2004 | Wong et al. |
| 2005/0054991 A1 | 3/2005 | Tobyn et al. |
| 2006/0124662 A1 | 6/2006 | Reynolds et al. |
| 2006/0127425 A1 | 6/2006 | Walls et al. |
| 2006/0242780 A1 | 11/2006 | Yang et al. |
| 2009/0039177 A1 | 2/2009 | Bourhis |
| 2009/0206174 A1 | 8/2009 | Arnaud et al. |
| 2010/0147883 A1 * | 6/2010 | Fedorov ............... B05B 7/2416 |
| | | 239/340 |
| 2010/0170964 A1 | 7/2010 | Fedorov |
| 2010/0287991 A1 | 11/2010 | Brown et al. |
| 2011/0106021 A1 | 5/2011 | Ruegg et al. |
| 2011/0118694 A1 | 5/2011 | Yodfat et al. |
| 2011/0248052 A1 | 10/2011 | Kelly et al. |
| 2013/0092285 A1 | 4/2013 | Feriani et al. |
| 2013/0245604 A1 | 9/2013 | Kouyoumjian et al. |
| 2013/0296807 A1 | 11/2013 | Lintern et al. |
| 2015/0021364 A1 | 1/2015 | Zehnder et al. |
| 2015/0201791 A1 | 7/2015 | Tinkler et al. |
| 2015/0335586 A1 | 11/2015 | Baruzzi et al. |
| 2016/0022011 A1 | 1/2016 | Rabe et al. |
| 2016/0192760 A1 * | 7/2016 | Nishiura ............... B05B 7/2416 |
| | | 239/337 |
| 2017/0051480 A1 | 2/2017 | Farcet et al. |
| 2017/0151362 A1 | 6/2017 | Edwards et al. |
| 2017/0340087 A1 | 11/2017 | Samain et al. |
| 2018/0050354 A1 | 2/2018 | Delsard |
| 2018/0318642 A1 | 11/2018 | Lunz et al. |
| 2019/0015857 A1 | 1/2019 | Gouchtchina et al. |
| 2020/0315319 A1 | 10/2020 | Samain |
| 2021/0178135 A1 | 6/2021 | Brinkman et al. |
| 2021/0307484 A1 | 10/2021 | Gouchtchina et al. |
| 2023/0123741 A1 | 4/2023 | Gouchtchina et al. |

FOREIGN PATENT DOCUMENTS

| | | |
|---|---|---|
| CN | 206228711 U | 6/2017 |
| CN | 208004186 U | 10/2018 |
| EP | 2123318 A1 | 11/2009 |
| EP | 2308603 A1 | 4/2011 |
| EP | 2433656 A1 | 3/2012 |
| JP | 2006198201 A | 8/2006 |
| JP | 3215873 U | 4/2018 |
| KR | 20120108252 A | 10/2012 |
| KR | 20120132067 A | 12/2012 |
| KR | 20130130569 A | 12/2013 |
| TW | I564484 B | 12/2003 |
| WO | 2008058160 A2 | 5/2008 |
| WO | 2015191014 A1 | 12/2015 |
| WO | 2016046385 A1 | 3/2016 |
| WO | 2017080685 A1 | 5/2017 |
| WO | 2019148116 A1 | 8/2019 |

OTHER PUBLICATIONS

U.S. Appl. No. 29/837,791, filed May 9, 2022, Gouchtchina.
U.S. Appl. No. 29/837,813, filed May 9, 2022, Gallar.
U.S. Appl. No. 29/837,826, filed May 9, 2022, Gallar.
Anywhere Portable Bottle Humidifier, multitasky.com, [online], [site visited Oct. 18, 2023], Available from internet, URL: https://multitasky.com/products/the-anywhere-humidifier (Year: 2023).
Fenty Skin Hydra Vizor Invisible Moisturizer, sephora.com, customer review oldest Dec. 21, 2020 [online], [site visited Oct. 18, 2023], Available from internet, https://www.sephora.com/product/fenty-skin-hydra-vizor-moisturizer-broad-spectrum-spf-30-sunscreen-P467249 (Year: 2020).
Hydrogen Water Rejuvenating Instrument, aliexpress.us, customer review oldest Jul. 17, 2023 [online], [site visited Oct. 18, 2023], Available from internet, URL: https://www.aliexpress.us/item/3256804679918558.html (Year: 2023).
J Isu Li Fe Mini Portable Humidifier, amazon.com, first available Mar. 6, 2021 [online], [site visited Oct. 18, 2023], Available from internet, URL: https://www.amazon.com/J ISU LI FE-Humidifier-Humidifiers-Container-Diversity/dp/B08Y6NH6KH/ref=asc_df_B08Y6N H6KH (Year: 2021).

(56) References Cited

OTHER PUBLICATIONS

Kozhya Air, kickstarter.com, first available Nov. 13, 2017 [online], [site visited Oct. 18, 2023], Available from internet, URL: https://www.kickstarter.com/projects/748624652/kozhya-air (Year: 2017).
Le Mieux Ionized Oxygen in Fus er, lemieuxskincare.com, customer review oldest Jul. 7, 2021 [online], [site visited Oct. 18, 2023], Available from internet, URL: https://lemieuxskincare.com/products/ionized-oxygen-infuser (Year: 2021).
Nano Spray Oxygen Injector Airbrush, temu.com, customer review oldest Jul. 29, 2023 [online], [site visited Oct. 18, 2023], Available from internet, URL: https://tinyurl.com/44n3f7ua (Year: 2023).
RIES The Essential Refillable Travel Container, sephora.com, customer review oldest Aug. 9, 2022 [online], [site visited Oct. 13, 2023], Available from internet, URL: https://www.sephora.com/product/the-essential-refillable-travel-container-P501801?skuld=2612455 (Year: 2022).
Search Report received in International Application No. PCT/US22/46510 dated Aug. 14, 2023, 5 pages.
Written Opinion received in International Application No. PCT/US22/46510 dated Aug. 14, 2023, 7 pages.

* cited by examiner

DERMAL SPRAY APPARATUS WITH DISPOSABLE CARTRDIGE AND METHOD

FIELD OF THE INVENTION

This application relates to dermal spray devices that utilize disposable cartridges, the disposable cartridges containing fluid that is dispensed by the spray devices.

BACKGROUND OF THE INVENTION

Skin care is very important. Many are turning to plant based and natural remedies. Certain plant-derived constituents can protect skin from deleterious effects, carcinogens, and a variety of chemical interactions. This concept has much scientific backing.

Human skin includes the epidermis, dermis and subcutis. The epidermis includes the stratum corneum and an underlying pigment layer. The stratum corneum is the outer layer of skin that protects the body. It is composed primarily of layers of dead, flattened keratinocytes surrounded by a phospholipid matrix. This acts in a similar as brick and mortar wall and functions to provide barrier to a microbial parasites as well as environmental toxins. The stratum corneum also presents a significant barrier to the delivery of transdermal drugs, vitamins, minerals, nutraceuticals and cosmeceuticals.

There are two major transdermal pathways. One is the intercellular route, which includes the movement of topically applied products around the cells of the stratum corneum via a phospholipid matrix that surrounds the cells. This is a tortuous path, so there are challenges to optimizing the speed of delivery and efficacy of skin-improving substances.

The other pathway is the transcellular pathway, which includes skin-improving substances directly passing through the cytoplasm of the dead keratinocytes of the stratum corneum, as well as the phospholipids matrix surrounding the cells. This is a more direct pathway yet there are still many challenges.

In either case, spraying a formulated fluid at a controlled pressure, spray pattern, and flow rate way can enhance penetration through the stratum corneum, so that the beneficial substances in the formulated fluid can penetrate and nourish the dermis, and in some cases enter the vasculature directly through the skin.

In the case of cosmetics and medical skincare products, the spray pattern, flow rate and other delivery aspects can be adjusted to optimize delivery to a desired region of the skin. For example, certain cosmetics can be delivered to provide a uniform coating on top of the stratum corneum, certain pigmentation products may be designed to reach the pigment layer under the stratum corneum.

U.S. Pat. No. 10,252,283 to Gouchtchina and Gallar includes a dermal spray apparatus that allows a system and method for dermal spraying includes a portable, hand-held skin care device with disposable formulation capsules that spray a formulation onto the skin. The device is set to maximize absorption and provide professional and uniform quality of application. The device receives, clamps and identifies the formulation capsules and its contents. Control circuitry regulates the formulation delivery. This assures the quantity, proportion, speed and timing of the application of the cosmetic formulation, including self-cleaning cycle operation and single button control logic. The capsule enables convenience and sterility from use of disposable capsules at home. Preferably the capsules contain a cosmetic formulation.

There remains a need to improve cartridge systems for use in dermal spray devices and system.

SUMMARY OF THE INVENTION

In one aspect, the invention involves a cartridge for dispensing a liquid comprising: a nozzle assembly, a liquid reservoir, and a cap attached to the liquid reservoir, wherein the cap is adapted to engage the nozzle assembly; the nozzle assembly comprising an inner body and an outer body, the inner body and outer body forming a first fluid passage therebetween, the first fluid passage adapted to deliver compressed air, the inner body comprising a second fluid passage in its interior, the second fluid passage adapted to deliver liquid from the liquid reservoir; wherein the nozzle assembly is moveable in a controlled direction relative to the cap; and the inner body of the nozzle assembly is adapted to pierce the liquid reservoir when the nozzle assembly is moved in the direction of the liquid reservoir to allow liquid from the liquid reservoir to flow into the second fluid passage.

The nozzle assembly of the cartridge may comprises a guide adapted to translate lateral motion into vertical motion for engaging the nozzle assembly with the liquid reservoir. The fluid reservoir of the cartridge may be a pouch and the cap seals the pouch. The cap may include recesses for capturing air bubbles in the fluid of the reservoir. The nozzle assembly may further comprise at least one guide flange adapted to guide movement of the nozzle assembly in a back and forth direction relative to the liquid reservoir. The guide flange, if used, is designed to guide movement of the nozzle assembly in a rotational direction relative to the liquid reservoir in addition to a back and forth direction relative to the liquid reservoir. The nozzle assembly may have a conical or rectangular shape, among others. In one aspect, the nozzle assembly has a rectangular shape and the first fluid path and second fluid path exit the nozzle assembly at about a 45 degree angle relative to the horizontal. In another aspect, the nozzle assembly comprises a first guide member and a second guide member, wherein the first guide member and second guide member are adapted to engage with the cap in a manner that permits the nozzle assembly to move in a controlled direction relative to the cap.

In another aspect, the invention relates to a dermal spray device for dispensing liquid from a cartridge, the dermal spray device comprising: a housing; a source of a compressed air; and a cartridge receiver, wherein the cartridge receiver is adapted to accept a cartridge including both a liquid container and a spray nozzle, wherein the dermal spray device dispenses liquid from the cartridge by supplying the compressed air to the nozzle of the cartridge, the nozzle assembly drawing liquid from the liquid container and mixing it with the compressed air. One or more of the features above related to the cartridge may be present in a cartridge that works with this dermal spray device.

The device may further comprise a sliding cover adapted to position the cartridge in the dermal spray device wherein the cartridge so positioned is capable of dispensing liquid through the spray nozzle. The sliding cover, if used, is adapted to engage with spray nozzle of the cartridge and activate the spray nozzle when the sliding cover is moved into an engaged position. The dermal spray device may include a base with an inductive charging element that allows for charging of a battery of the dermal spray device.

The device may further comprise a compressor for supplying compressed air to the spray nozzle. The cartridge receiver may comprise a fluid conduit in fluid communication with the compressor, wherein the fluid conduit is adapted to engage with the cartridge.

In another aspect, the invention relates to a method of spraying a liquid onto a user's skin using the dermal spray device comprising inserting the cartridge including both a liquid container and a spray nozzle in the dermal spray device; and directing a spray of the liquid from the liquid container through the spray nozzle toward the user's skin. The method may also include a step of closing a cover adapted to position the cartridge in the dermal spray device wherein the cartridge so positioned is capable of dispensing liquid through the spray nozzle. In one aspect, closing the cover may engage the spray nozzle by moving it toward the liquid container of the cartridge allowing liquid to flow into the spray nozzle.

In another aspect the invention involves a dermal spray system for dispensing liquid from a cartridge, the dermal spray device comprising: a housing; a source of a compressed air; a cartridge receiver, wherein the cartridge receiver is adapted to accept a cartridge; wherein the dermal spray device dispenses liquid from the cartridge by supplying the compressed air to the nozzle of the cartridge, the nozzle drawing liquid from the liquid container and mixing it with the compressed air; and wherein the cartridge comprises: a nozzle assembly, a liquid reservoir, and a cap attached to the liquid reservoir, wherein the cap is adapted to engage the nozzle assembly; the nozzle assembly comprising an inner body and an outer body, the inner body and outer body forming a first fluid passage therebetween, the first fluid passage adapted to deliver compressed air, the inner body comprising a second fluid passage in its interior, the second fluid passage adapted to deliver liquid from the liquid reservoir; wherein the nozzle assembly is moveable in a controlled direction relative to the cap; and the inner body of the nozzle assembly is adapted to pierce the liquid reservoir when the nozzle assembly is moved in the direction of the liquid reservoir to allow liquid from the liquid reservoir to flow into the second fluid passage.

DETAILED DESCRIPTION OF THE INVENTION

The present invention involves improvements to dermal spray systems that provide unique advantages for dermal and topical application.

Figure 1:
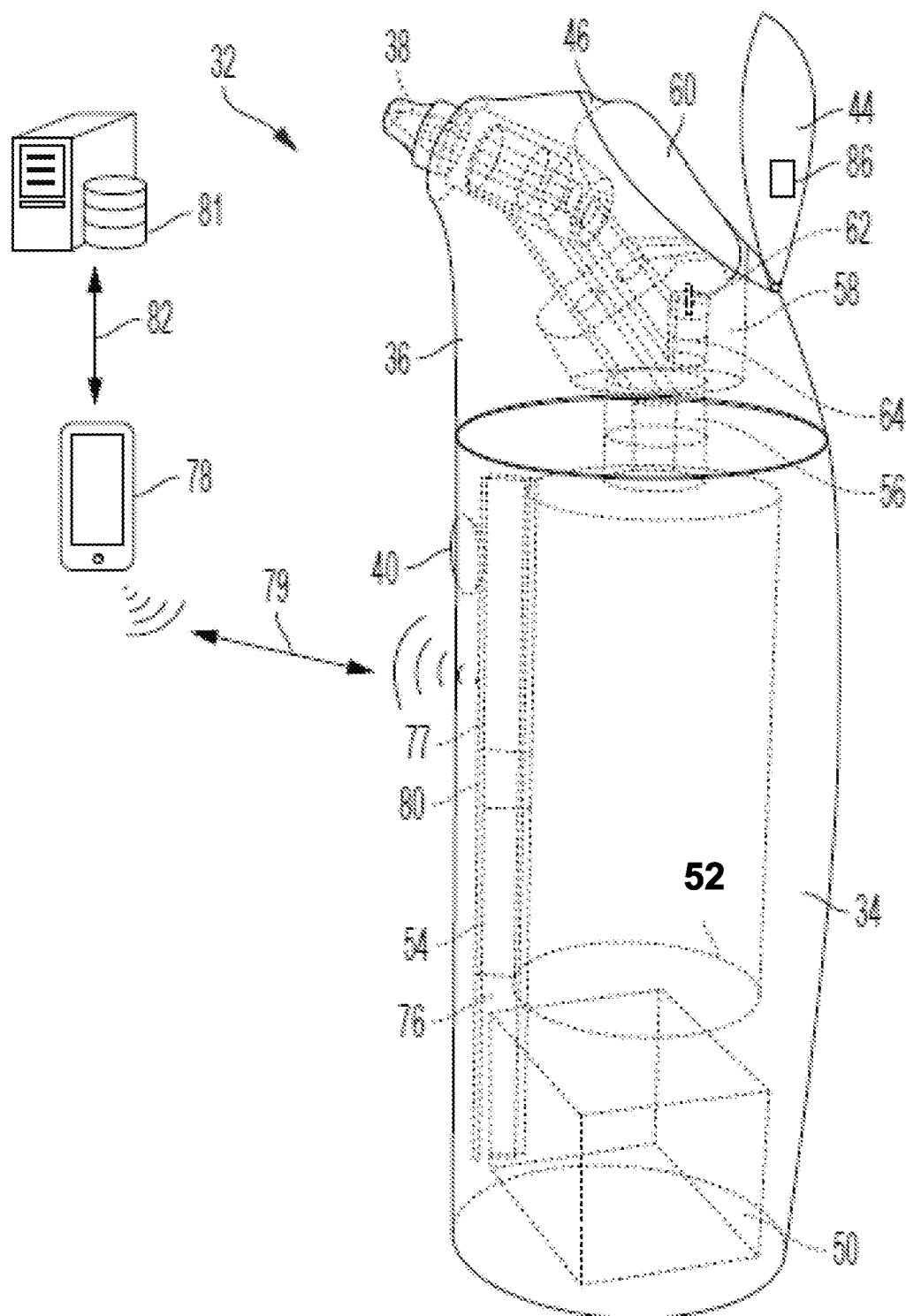
FIG. 1 shows a dermal spray apparatus.

FIG. 1 shows a dermal spray device 32 described in U.S. patent application Ser. No. 17/224,824, entitled "DERMAL SPRAY DEVICE AND METHOD", filed Apr. 7, 2021. Hidden lines are used to reveal the internal components of the device 32. The device includes a spray head 36, including a nozzle 38, and a body 34. The body 34 includes a pressure source 52 such as an air compressor that can be used to propel a dermal composition supplied in a container 60 when the user presses a button 40 mounted on the body 34.

The device 32 includes a battery 50, control circuitry 54, a data storage unit 76, a data transmission unit 77 that is configured to permit data transmission of device data 79 to and from a mobile device 78, such as a smartphone. The mobile device 78 can communicate with a server 81 using a secure internet connection 82, to communicate user device data between the server and mobile device. The mobile device 78 is configured (a) to combine the device data with secure user data into user device data, and (b) to display the user device data to the user. The mobile device may send anonymized user device data to the server, which can be used to build a database that can be utilized in several machine learning processes of aid in the selection of serums. The device also includes an accelerometer 80 and an encoding identification unit 86.

The capsule 60 is inserted into a compartment 46 the dermal spray device 32. The compartment 60 includes a door 44 and a capsule nest 58 for holding the capsule in place. A needle 62 penetrates the capsule 60 and allows the contents of the capsule to be drawn toward the nozzle 38. Air from a pressure chamber 64 is routed to the nozzle through a pressurized conduit 56. Further details regarding the dermal spray device and its use may be found in U.S. patent application Ser. No. 17/224,824, incorporated above. The inventors have perceived a need to improve the spray device 32 in several respects.

The present inventors have perceived a need to provide a cartridge system for a dermal spray device that has one or more of the following features. In one aspect, the cartridge is capable of being stored and easily pierced at the time of use. In another aspect, the cartridge may be easily inserted into a spray device and activated after it is positioned within the spray device. In another aspect, the cartridge has a disposable nozzle that eliminates or reduces the need for cleaning of the dermal spray device. In another aspect, the cartridge is capable of being filled and dispensed without air pockets interfering with the consistent dispensing of contents.

A cartridge is provided for dispensing a liquid from a dermal spray device, wherein the cartridges includes a nozzle assembly, a fluid reservoir, and a cap attached to the fluid reservoir that is adapted to engage the nozzle assembly. The cartridge includes a disposable nozzle assembly that is attached to the cartridge. When the cartridge is inserted into the device the nozzle assembly is moved into a position that allows an inner body, e.g., a needle, to pierce a reservoir and allow liquid to enter the nozzle assembly.

A cartridge 200 according to one aspect of the invention is shown in FIGS. 2A-G. The cartridge 200 includes a reservoir body 202, a reservoir cap 201 and to which a nozzle assembly is attached. The nozzle assembly includes an outer nozzle body 208 and an inner nozzle body 220. The inner nozzle body 220 is rigidly attached to the outer nozzle body 208. The inner nozzle body 220 preferably has a tapered outer surface 221, and the outer nozzle body 208 has a tapered inner surface 225. The space between the outer surface 221 of the inner nozzle body 220 and the inner surface 225 of the outer nozzle body 208 form a fluid passage of the nozzle assembly for delivering compressed air. Compressed air is provided into the passage through a fluid attachment point 224. The inner nozzle body 220 has a first end 226 and a second end 223, the second end being adapted to pierce a seal in the reservoir body 202 and provide liquid material from the reservoir body (e.g., a liquid-containing pouch) to the spray nozzle.

Figure 2A:
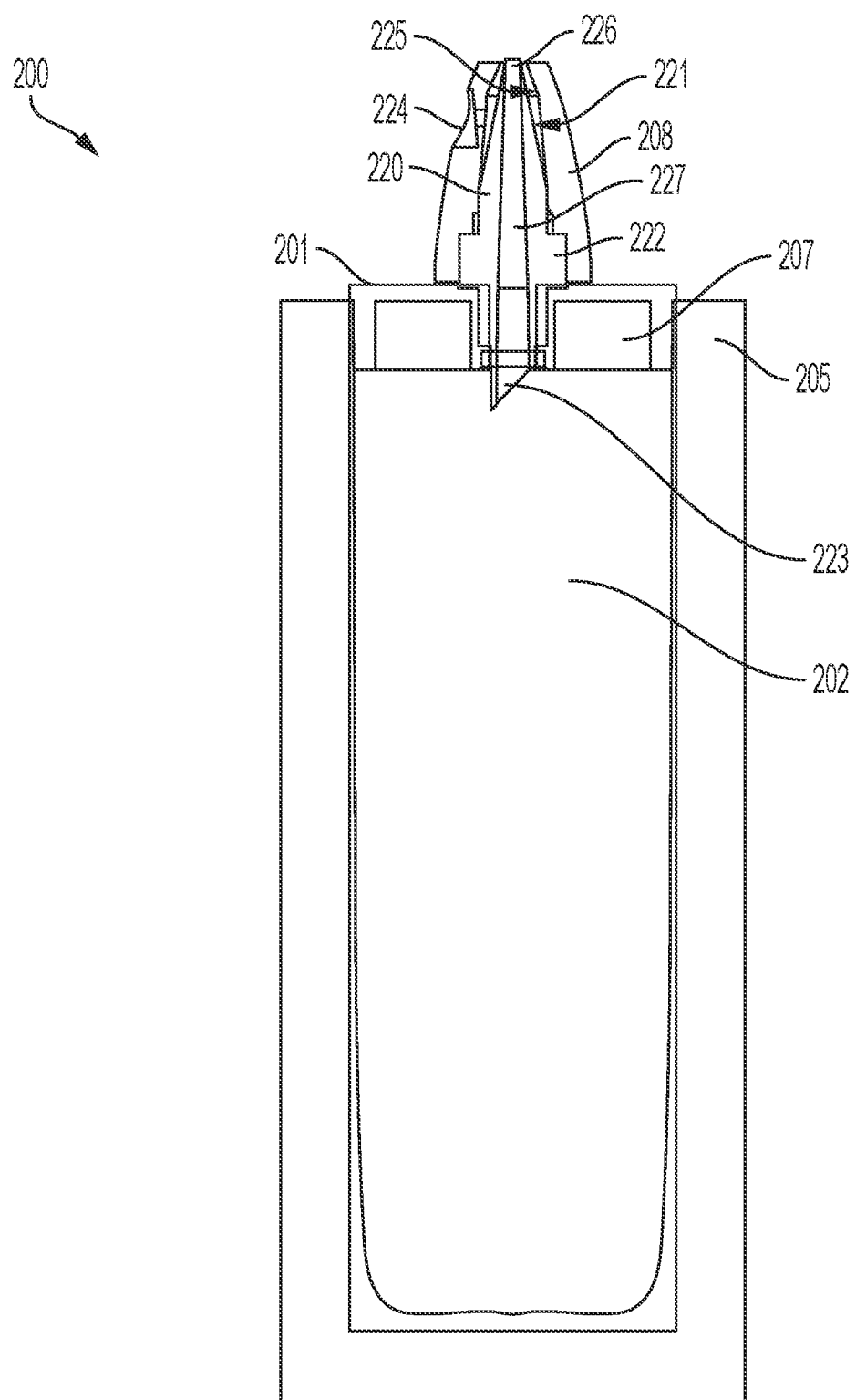
FIG. 2A shows a dermal spray cartridge according to an embodiment of the invention.
Figure 2B:
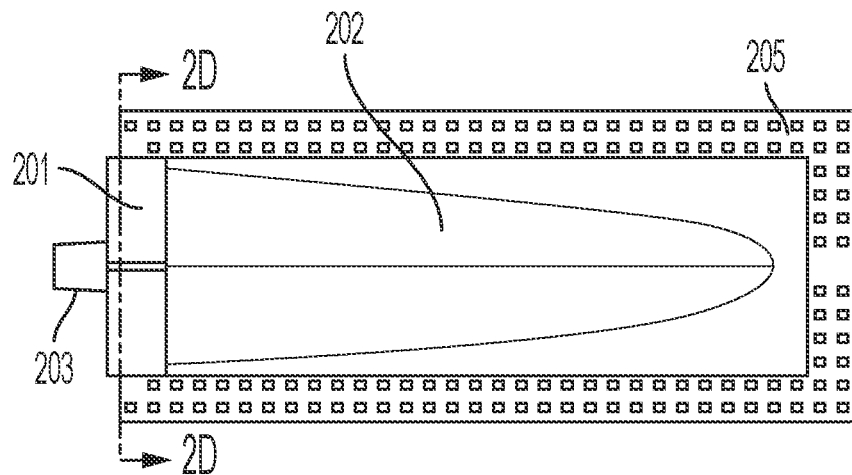
FIG. 2B shows a first side view of a pouch-type reservoir which forms part of a cartridge according to an embodiment of the invention.
Figure 2C:
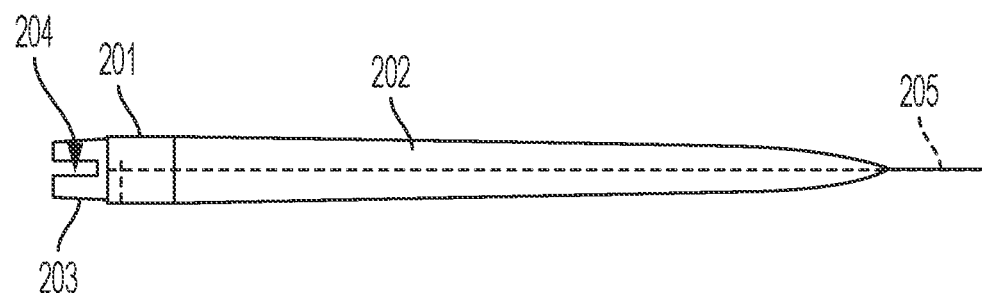
FIG. 2C shows a second side view of a pouch-type reservoir which forms part of a cartridge according to an embodiment of the invention.
Figure 2D:
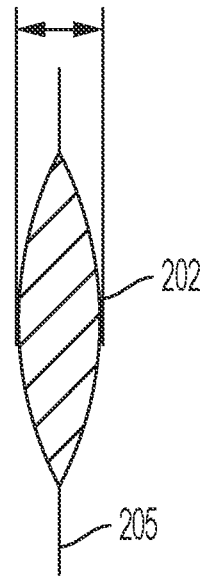
FIG. 2D shows a bottom view of a pouch-type reservoir which forms part of a cartridge according to an embodiment of the invention.
Figure 2E:
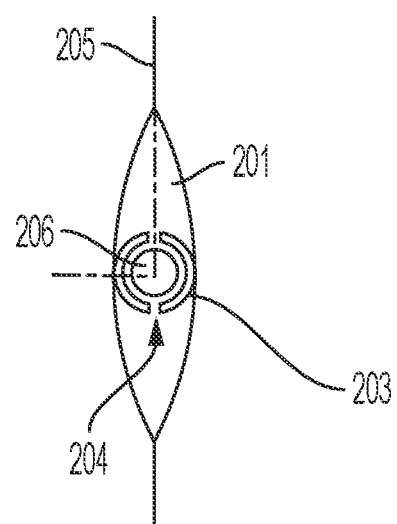
FIG. 2E shows a top view of a pouch-type reservoir which forms part of a cartridge according to an embodiment of the invention.
Figure 2F:
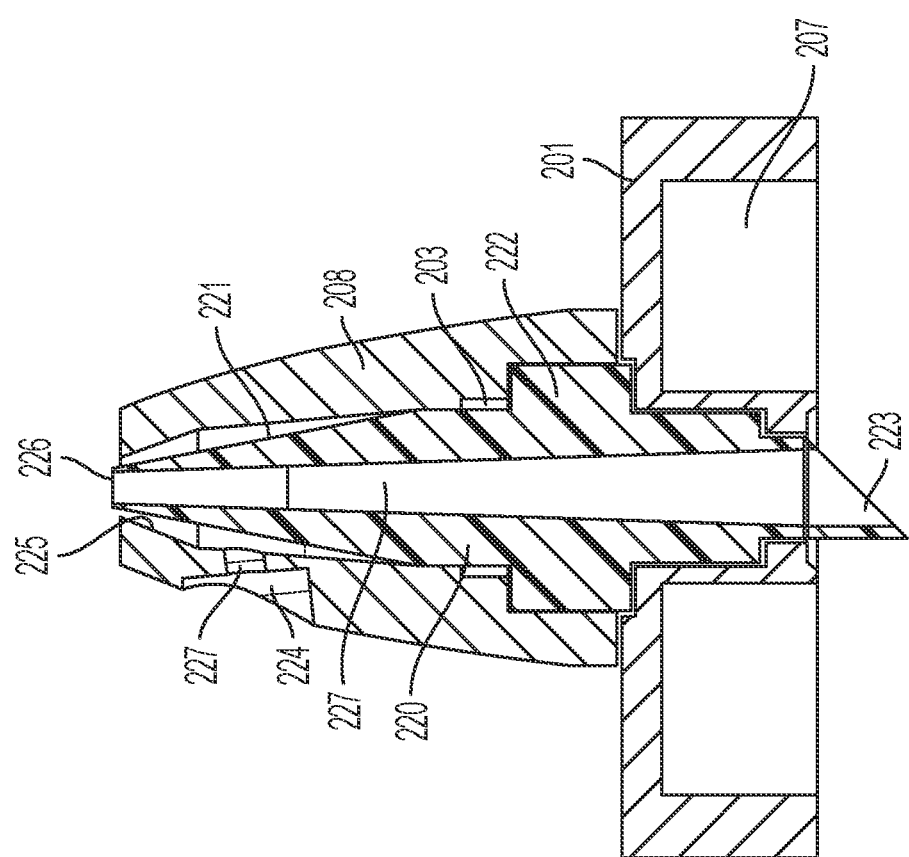
FIG. 2F shows a side view of a nozzle assembly according to an aspect of the invention.

FIGS. 2B-E show aspects of the reservoir body 202 of the cartridge 200. This includes a reservoir cap 201 and flat edges 205. Also provided is guide post 203 adapted to receive the nozzle assembly shown in FIG. 2A. The reservoir cap 201 includes a reservoir cap recess 207 as shown in FIG. 2F. As shown in FIGS. 2C and 2E, the guide post 203 includes a guide slot 204 that is adapted to define a controlled sliding movement of the inner nozzle body 220 through the opening 206 relative to the reservoir body 202. This movement is used to allow the second end 223 of the inner nozzle 220 to pierce the reservoir body 202. If desired, the guide slot may include curvature so that the nozzle assembly rotates by for example 90 degrees while it is being engaged.

FIG. 2F shows the details of the nozzle assembly when it is slid into the engaged position relative to reservoir body. The fluid attachment point 224 includes a passage 227 linking it to the recess between the outer nozzle body 208 and the inner nozzle body 220. Portions of the guide post 203 are shown projecting above the guide flanges 222. The inner nozzle body 220 and outer nozzle body 208 can be made by injection molding of rigid plastic materials. It is important for the materials to be strong enough to maintain precise tolerances of the fluid passage, and allow for movement of the inner nozzle body 220 and outer nozzle body 208 relative to the fluid reservoir 201.

Figure 2G:
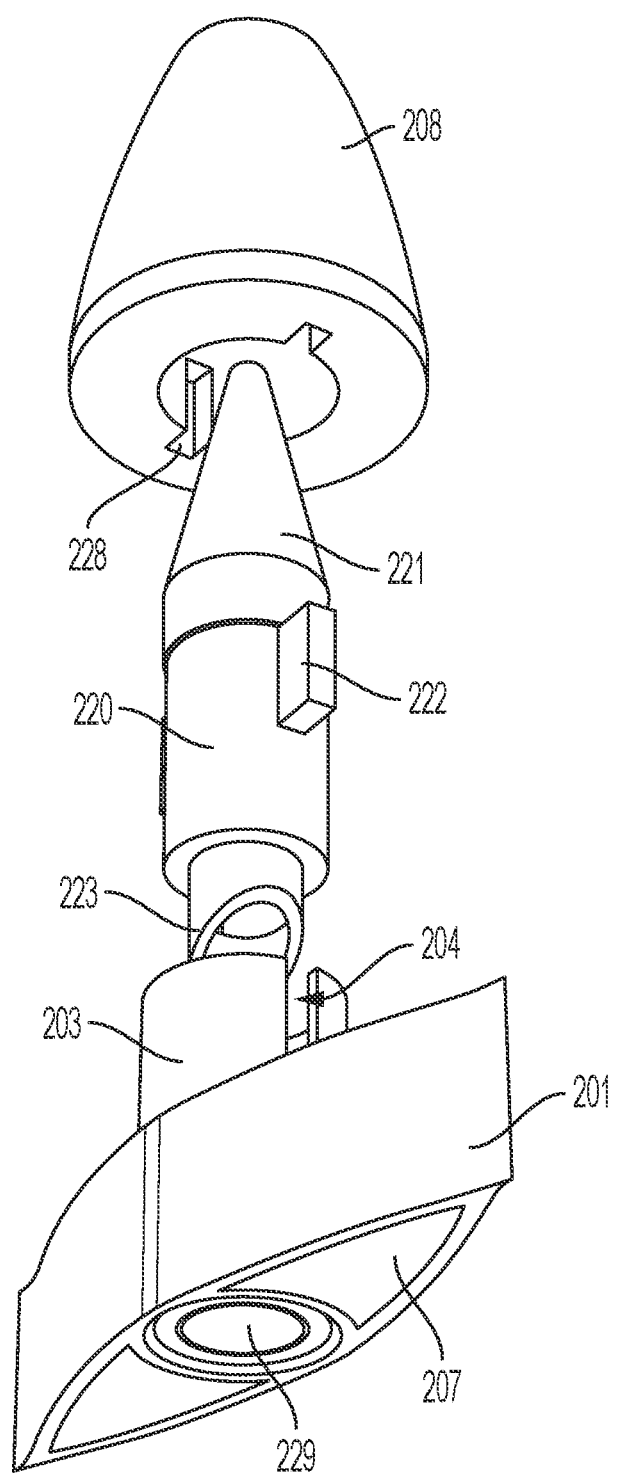
FIG. 2G shows a perspective view of a nozzle assembly according to an aspect of the invention.

FIG. 2G shows a perspective view of the nozzle assembly. It should be noted that the guide flanges 222 may be seated in the outer nozzle body 208 by insertion into the nozzle body recesses 228. The seal 229 is shown in the reservoir cap 201 in FIG. 2G. The seal 229 may be made of a material that can be readily pierced by the second end 223 of the inner nozzle body 220. While the flange 222 and guide slot 204 are pictured in a form that is adapted for back and forth motion of the nozzle assembly, other configurations are possible. For example the guide flange may be provided in cylindrical form and the notch designed to permit both back and forth movement as well as twisting movement. In one instance, the nozzle assembly may be configured to rotate by a desired amount such as 45 degrees or 90 degrees such that the inner nozzle body pierces the seal 229 at the end of the motion, allowing the liquid contents of the fluid reservoir to move into the fluid passage within the inner nozzle body.

Figure 3:
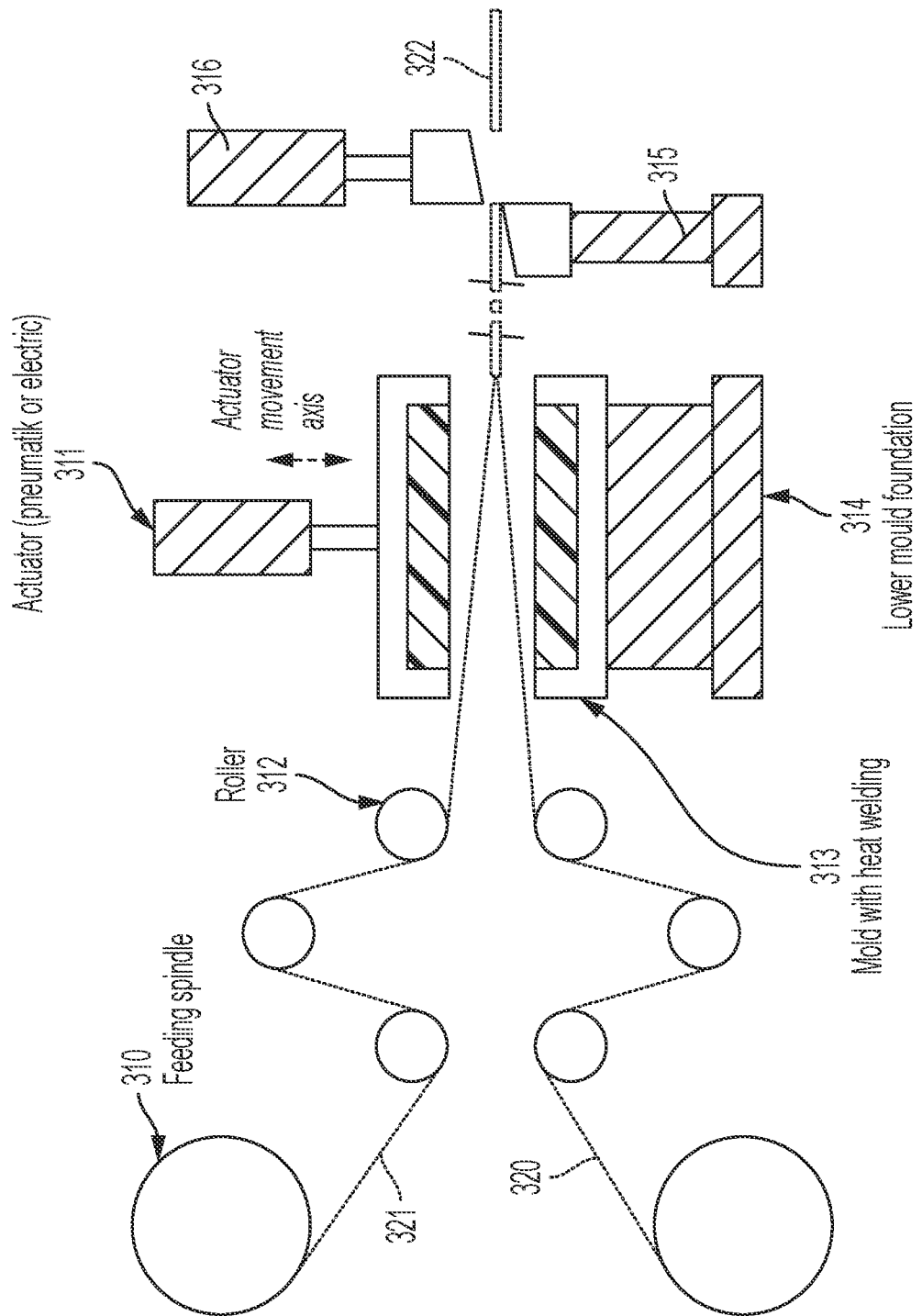
FIG. 3 shows a diagram of an exemplary process for making a pouch-type reservoir to be used with a cartridge according to an aspect of the invention.

In one aspect, fluid reservoirs may be manufactured using a process as shown in FIG. 3. A bottom film 320 and top film 321 are fed from respective feeding spindles 310 through a series of rollers 312 into a mold for heat welding 313. The mold 313 may include a lower mold foundation 314 and an actuator 311 which opens and closes the mold. A cutter including a bottom cutting element 315 and top cutting element 316 can be intermittently engaged to cut away finished pouches 322 of each fluid reservoir. While this method is advantageous for the rapid production of a larger number of reservoirs other techniques may be used to manufacture a fluid reservoir. In addition, it is possible to use different types or reservoirs with the cartridges of the present invention.

In one aspect, one or both of the bottom film 320 and top film 321 used to make the reservoir is a flexible plastic film that allows the reservoir to collapse as fluid is withdrawn from the reservoir. For example, the film may be a polyethylene terephthalate (PET) film having a thickness of between 40-50 microns. In one aspect, the film may include two or more layers of film that are adhered together. In this case, a radio frequency identification (RFID) tag or other information containing device may be positioned between separate layers of a multilayer film that makes up the reservoir. The RFID tag may include information about the dermal serum or material contained within the cartridge that may be read by the dermal spray device upon insertion of the cartridge into the device. In another aspect, the cartridge may contain a barcode, NFC, QR code or other information containing mechanism that is read by the dermal spray device.

FIGS. 4A-F show a cartridge and system according to another aspect of the invention, wherein the nozzle assembly has a 45 degree bend. The angle of the bend may range from 0 degrees to 90 degrees, and can depend on the geometry of the dermal spray device. The cartridge 400 includes a reservoir cap 401, reservoir body 402, and nozzle body 408. The reservoir cap 401 has a guide post 403 that includes guide slots 404 on either side to allow for up and down movement of the nozzle assembly relative to the reservoir body 402. The reservoir body may have flat edges 405 around its periphery.

Figure 4A:
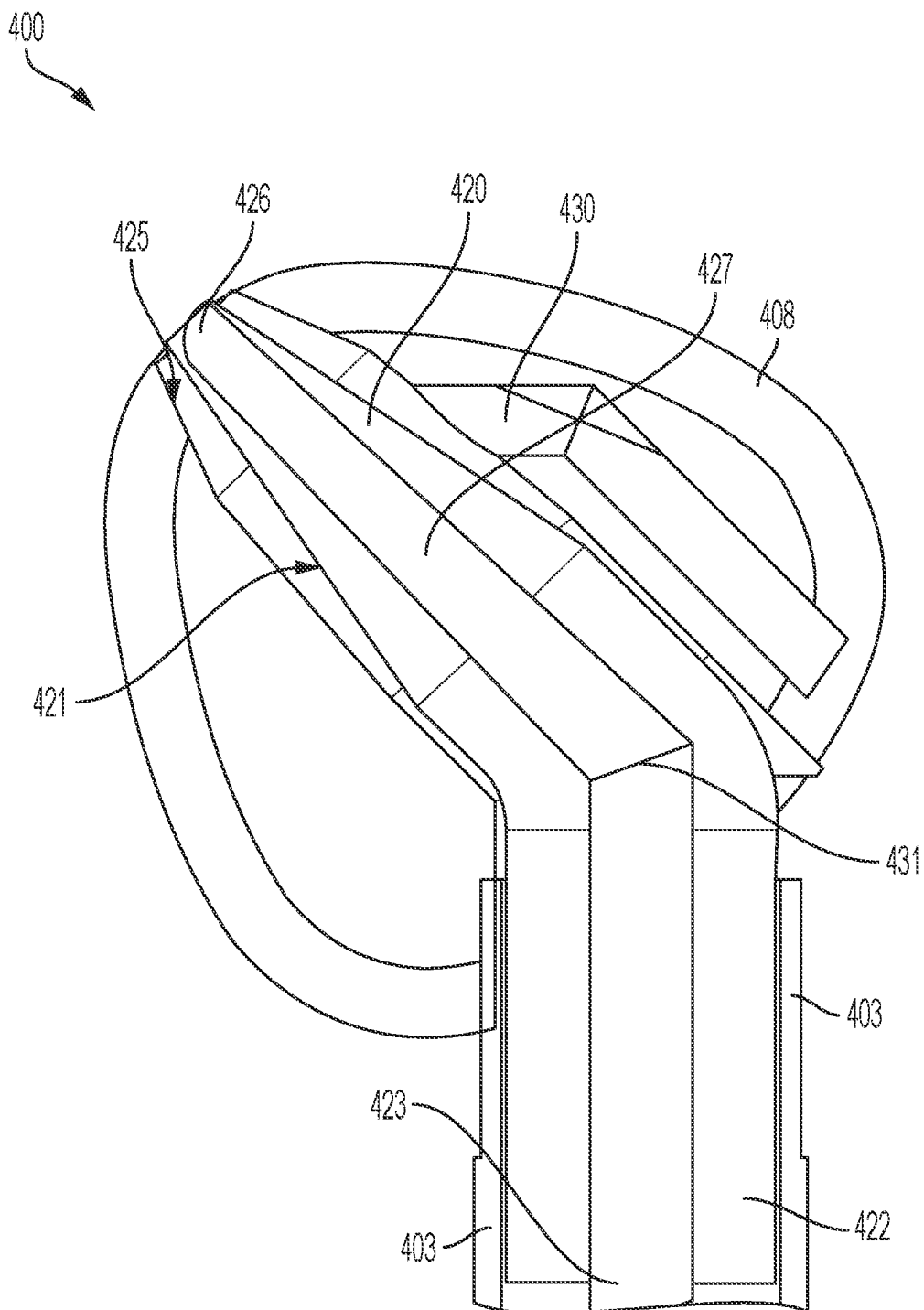
FIG. 4A shows a nozzle having a 45 degree bend according to an aspect of the invention.
Figure 4B:
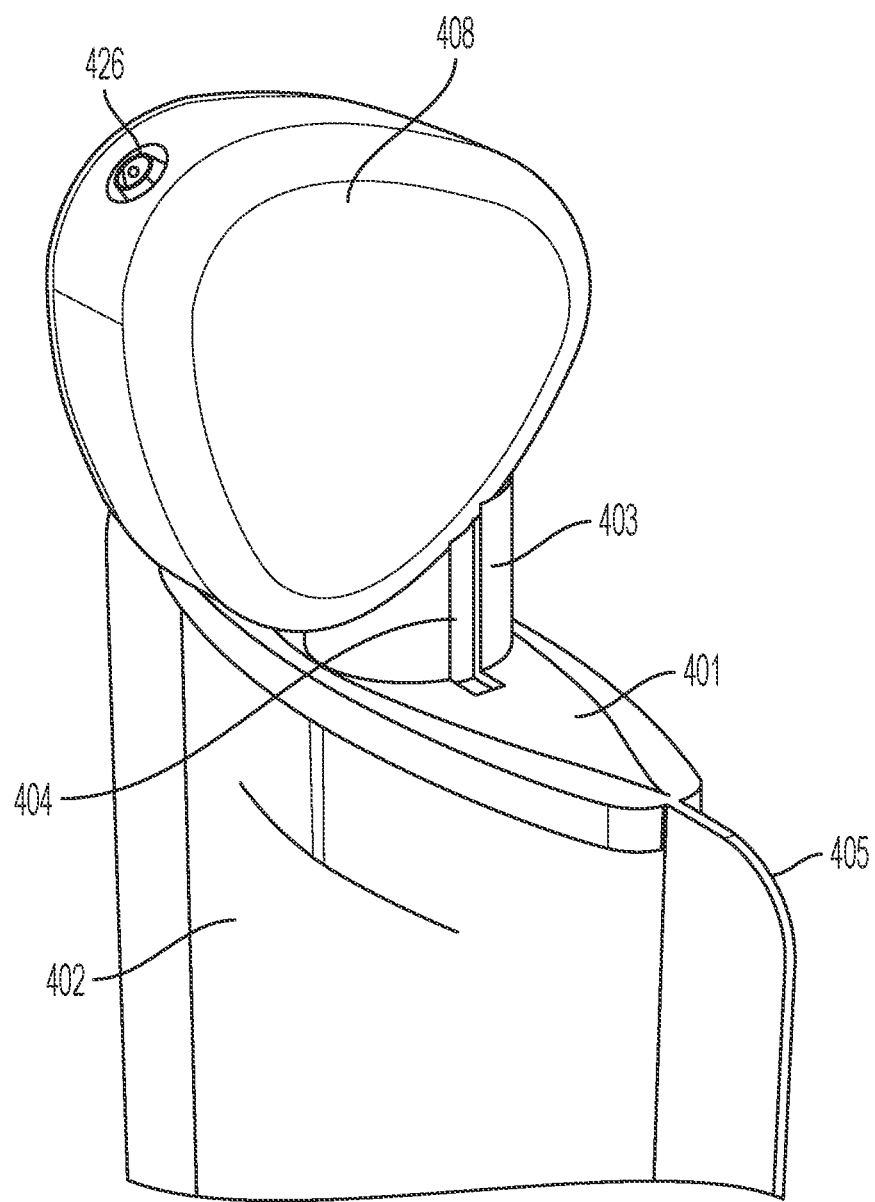
FIG. 4B shows a dermal spray cartridge having the nozzle of FIG. 4A according to an embodiment of the invention.
Figure 4C:
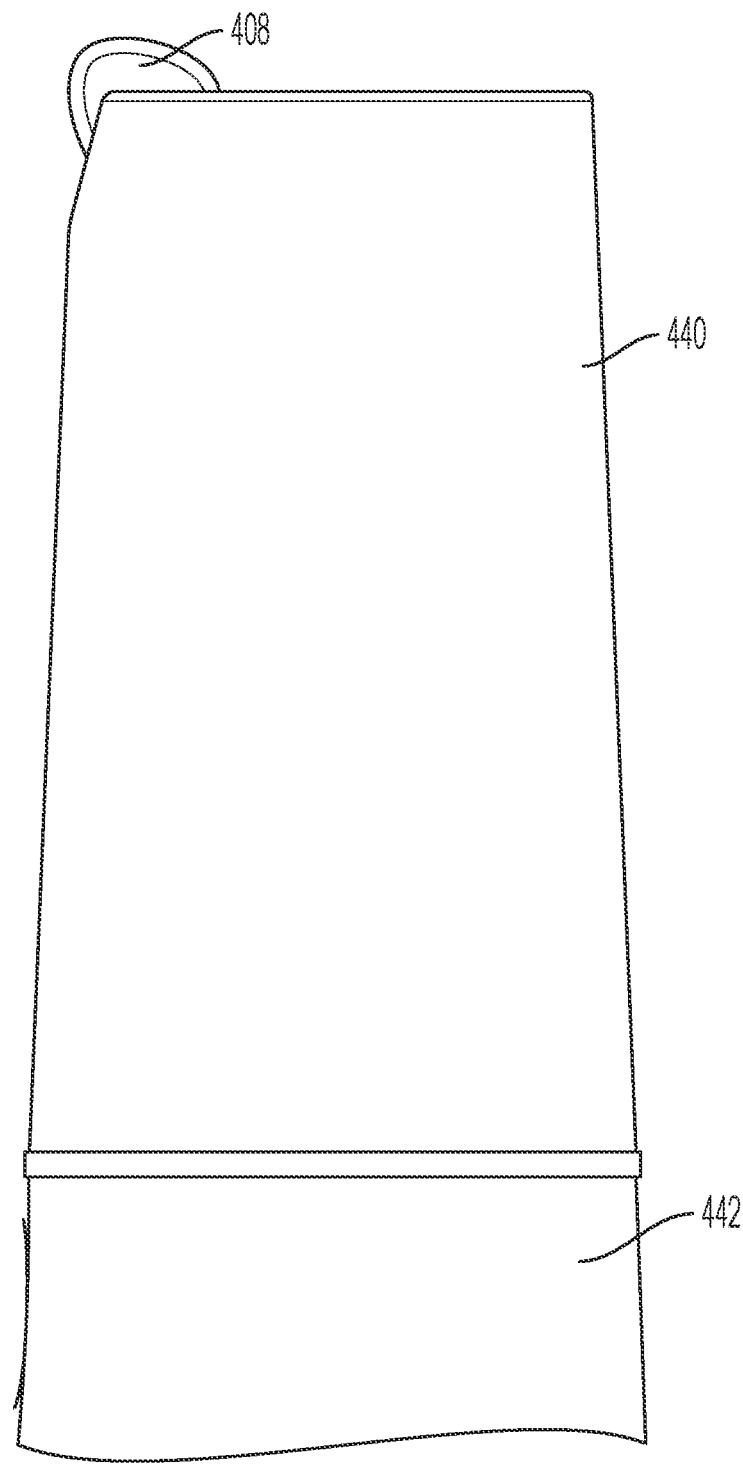
FIG. 4C shows a perspective view of an exemplary dermal spray device incorporating the nozzle of FIG. 4A.
Figure 4D:
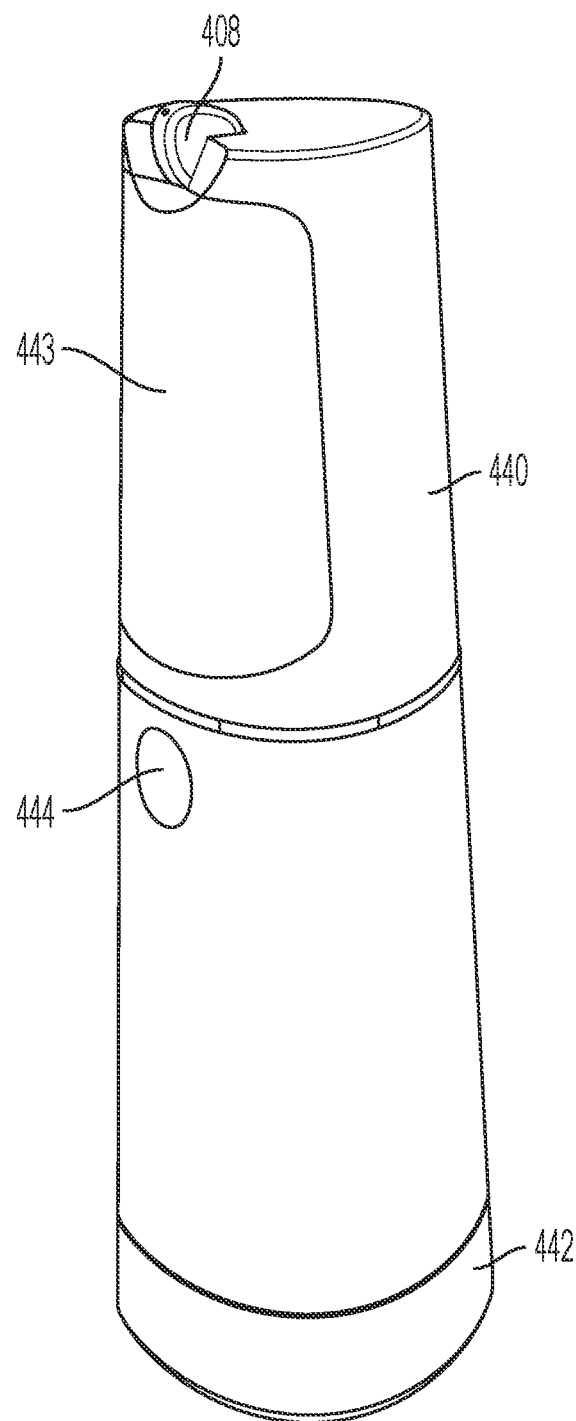
FIG. 4D shows a perspective view of an exemplary dermal spray device incorporating the nozzle of FIG. 4A.
Figure 4E:
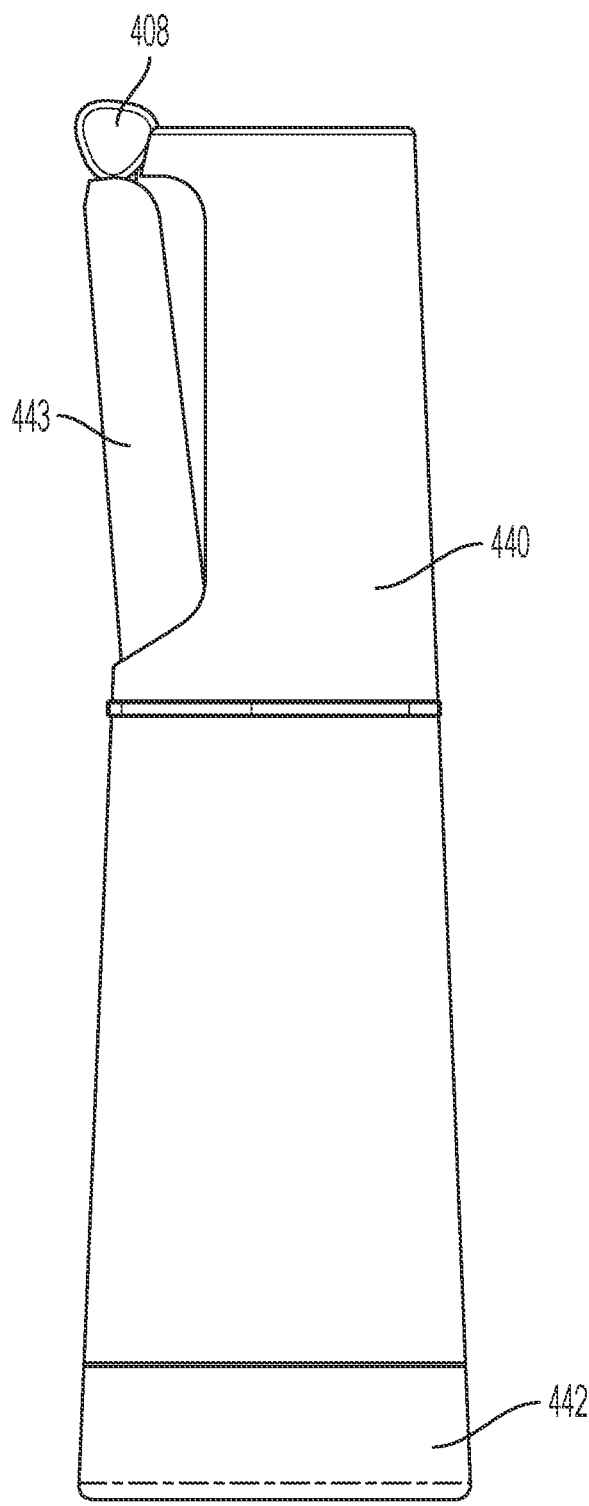
FIG. 4E shows a side view of an exemplary dermal spray device incorporating the nozzle of FIG. 4A with a cartridge door in an open position.
Figure 4F:
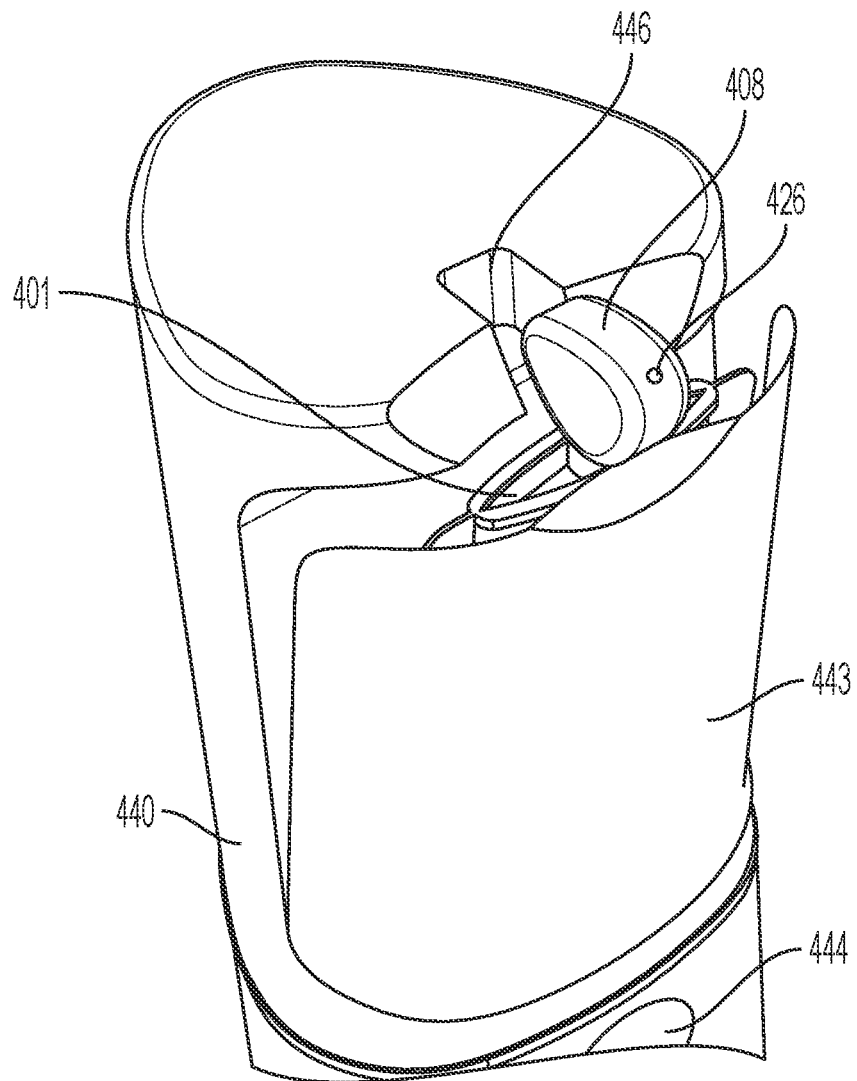
FIG. 4F shows a perspective view of an exemplary dermal spray device incorporating the nozzle of FIG. 4A with a cartridge door in an open position.

The nozzle assembly includes an inner nozzle body 420 having a tapered outer surface 421 and a guide flange 422. The inner nozzle body 420 has a first end 426 and a second end 423. The outer nozzle body 408 includes a tapered inner surface 425 and the inner nozzle body 420 has a tapered outer surface 421. These surfaces form an air passage to the nozzle through fluid passage 430. Fluid moves from the reservoir through the fluid passage 427 through the inner nozzle body 420. The fluid passage includes a bend 431. The bend 431 is shown having an angle but may also be smooth. FIG. 4B shows a cartridge including the nozzle shown in FIG. 4A. The cartridge includes a nozzle body 408, which is attached to a fluid reservoir 402 having flat sides 405 by way of a guide post 403 with guide slot 404 being provided on a reservoir cap 401.

FIG. 4C-F shows how a the nozzle body 408 assembled on a dermal spray device. The dermal spray device has a handle body 440 and a handle base 442. The device includes a door 443 for insertion of a cartridge. The spray device includes a recess 446 that provides clearance of the nozzle body 408 when the cartridge is inserted into the spray device. The spray device may include a button 444 for activating the sprayer.

Figure 5A:
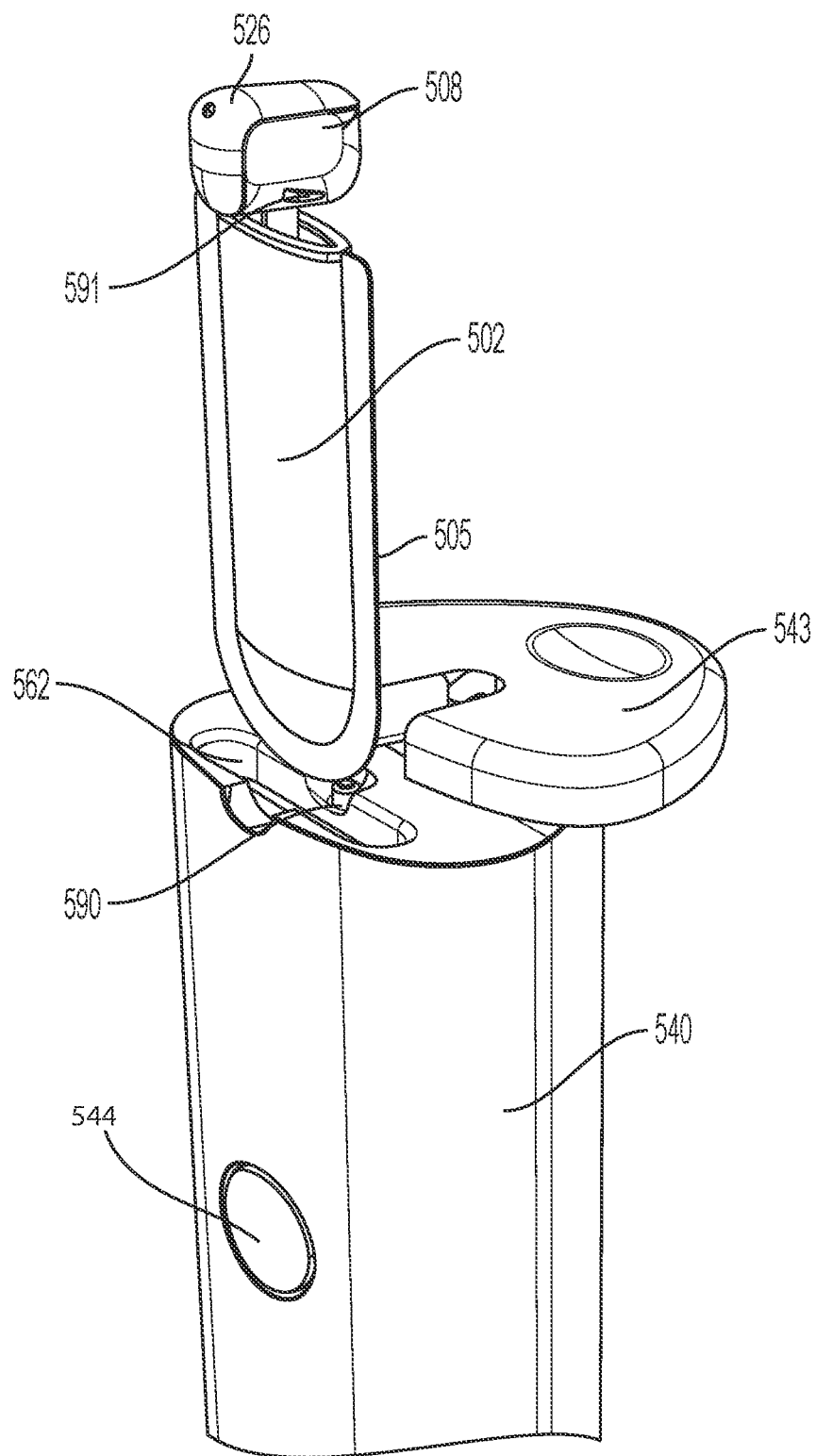
FIG. 5A shows a dermal spray cartridge having the nozzle with a 45 degree exit angle according to an embodiment of the invention.
Figure 5B:
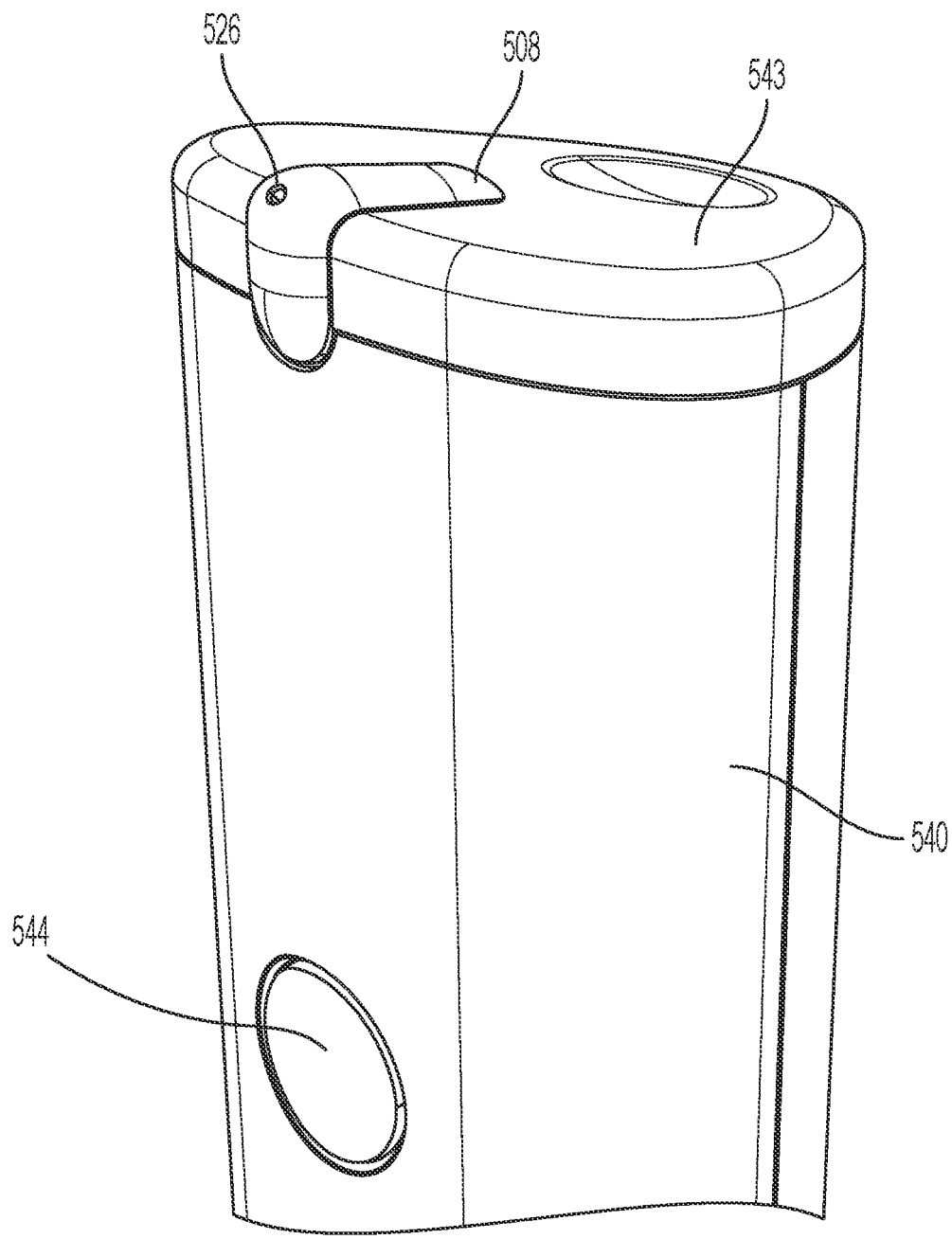
FIG. 5B shows a side view of an exemplary dermal spray device incorporating the nozzle of FIG. 5A where the cartridge is closed within the device.
Figure 5C:
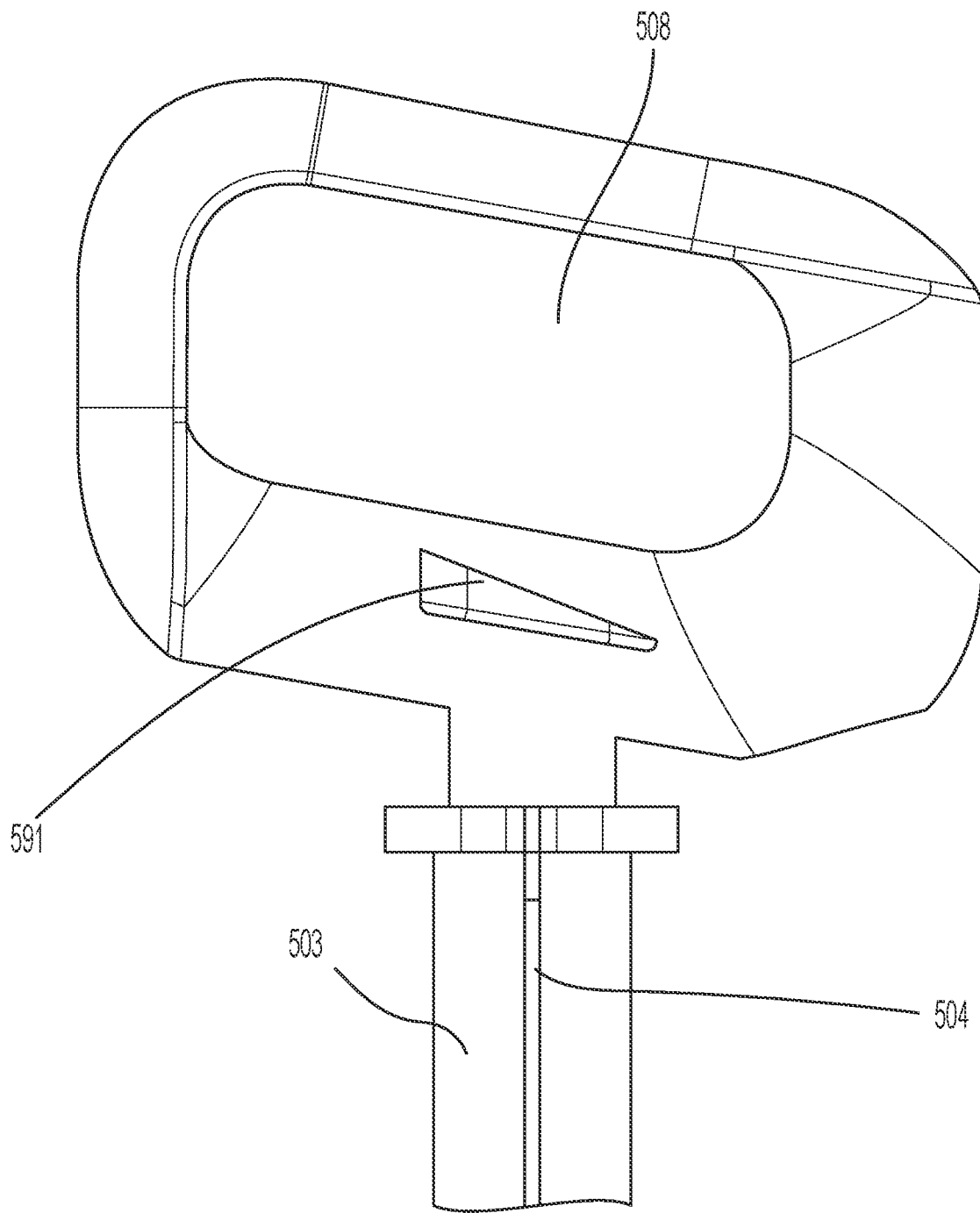
FIG. 5C shows a close up view of the nozzle body of the dermal spray cartridge of FIG. 5A.

FIG. 5A shows a cartridge having a nozzle body 508 that includes a nozzle outlet 526 that has a 45 degree angle 5 relative to the fluid reservoir 502. The fluid reservoir may include a flat edge 505 as described above. The nozzle body 508 includes a sloped guide 591 on both sides of the nozzle body. When the device cap 543 is slid laterally into position as shown in FIG. 5B, a cam or wing (not shown) on the underside of the device cap 543 engages with the sloped guide 591 and exerts a downward pressure on the outer nozzle body 508 and nozzle assembly. The downward force of the nozzle assembly allows the second end of the inner nozzle body to pierce the seal of the reservoir body 502 allowing the liquid from the reservoir body to be drawn into the fluid passage within the inner nozzle body. The nozzle body may include a guide post 503 that includes guide flanges 504 on either side to allow for up and down movement of the nozzle assembly.

The cartridge including the reservoir 502 and nozzle body 508 is inserted into a slot 562 in the handle body 540 of the dermal spray device. A button 544 is provided for activating the device. A connection 590 allows pressurized gas (e.g., compressed air) to flow into a fluid passage in the bottom of the nozzle body 508 that is directed to the tapered gap between the inner nozzle body and outer nozzle body. The fluid is typically pressurized air that mixes with fluid from the fluid reservoir 502 at or near the nozzle outlet 526.

Figure 5D:
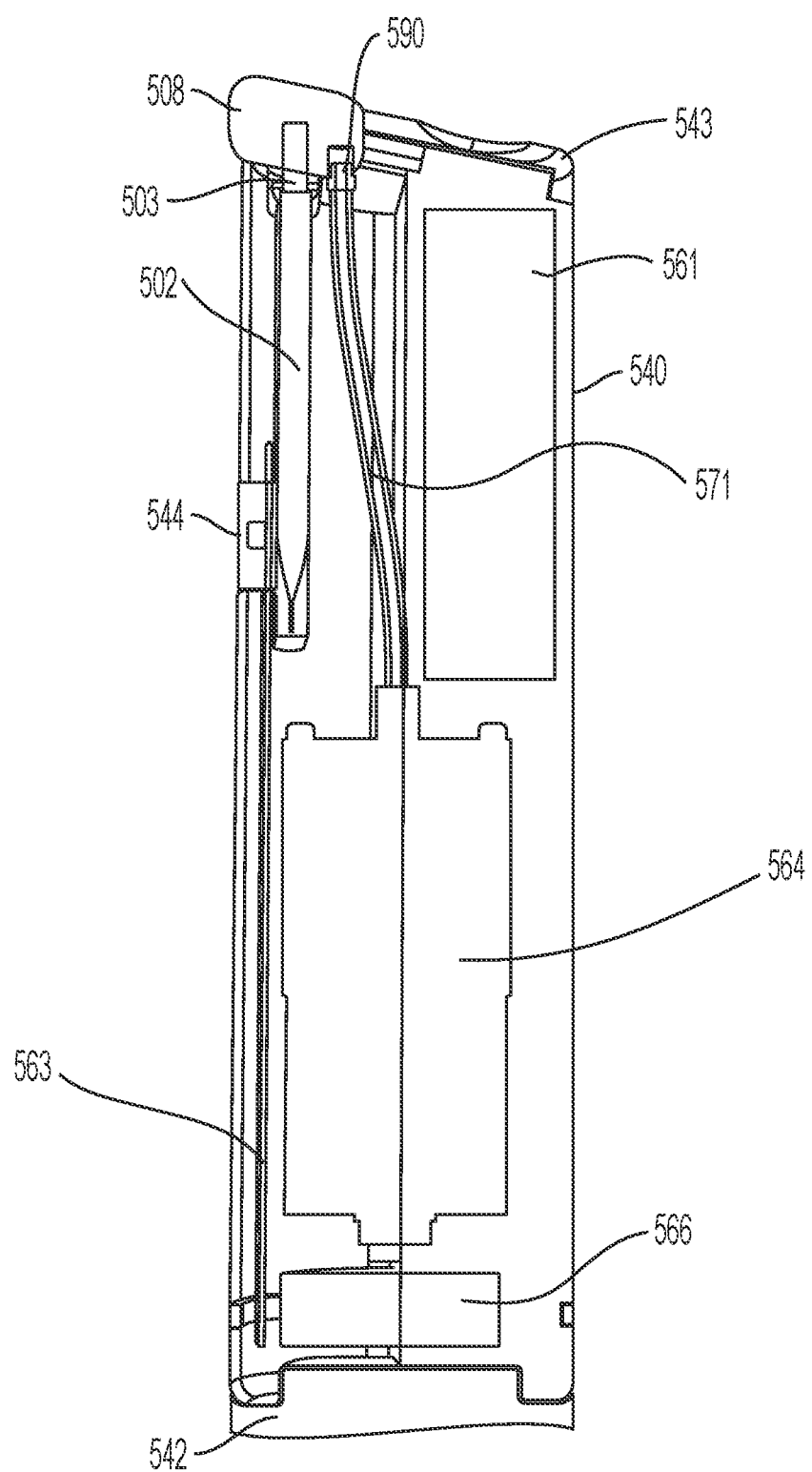
FIG. 5D shows a cross-sectional view of the dermal spray device of FIG. 5A.

FIG. 5D shows a cross section view that includes many of the elements discussed above. In addition to those elements, a battery 561 is shown in the handle assembly, and an induction coil 566 is shown near the base of the handle body. The induction coil cooperates with electric power transmitted through the base 542 to conveniently charge the device. An air compressor 564 is provided to supply compressed air to the nozzle body 508 through conduit 571. A PCB 563 is provided within the handle to provide control and other functionality to the dermal spray device.

Figure 6A:
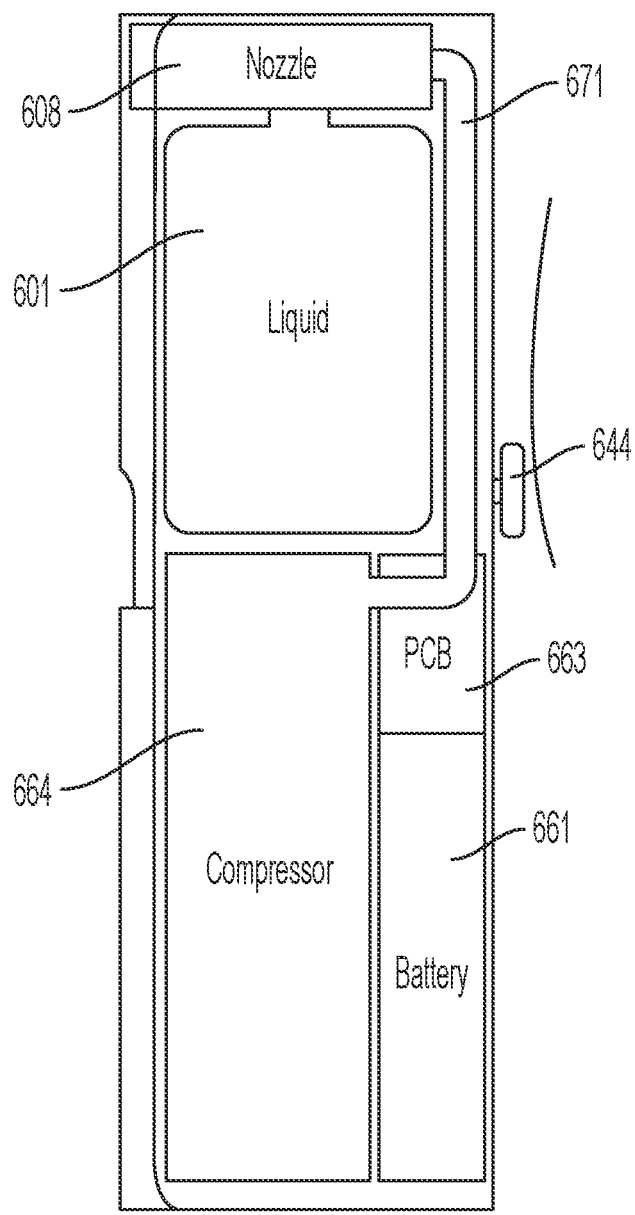
FIG. 6A shows a schematic view of a dermal spray device according to an aspect of the invention.
Figure 6B:
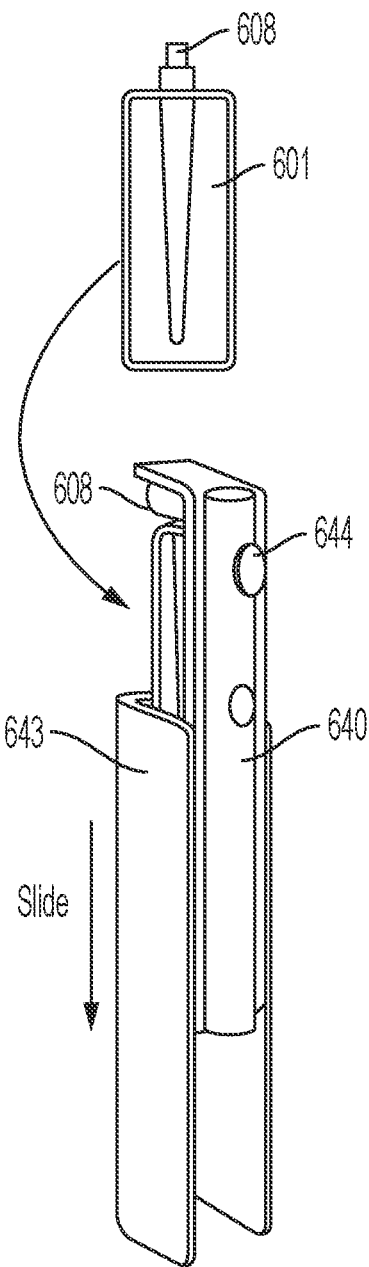
FIG. 6B shows a perspective view of the dermal spray device shown schematically in FIG. 6A.

FIG. 6A-B show a dermal spray device where a cartridge is inserted and positioned into place by a vertically sliding door 643. The device includes a nozzle body 608 connected to a reservoir 601, a compressor 664 and a fluid conduit 671 connecting the compressor 664 to the nozzle body 608. The device includes a button 644 for activating the spray, a printed circuit board 663 and a battery 661. A perspective view of the dermal spray device is shown in FIG. 6B showing the motion of the door 643 that encloses the cartridge within the handle body 640 of the dermal spray device.

Figure 7A:
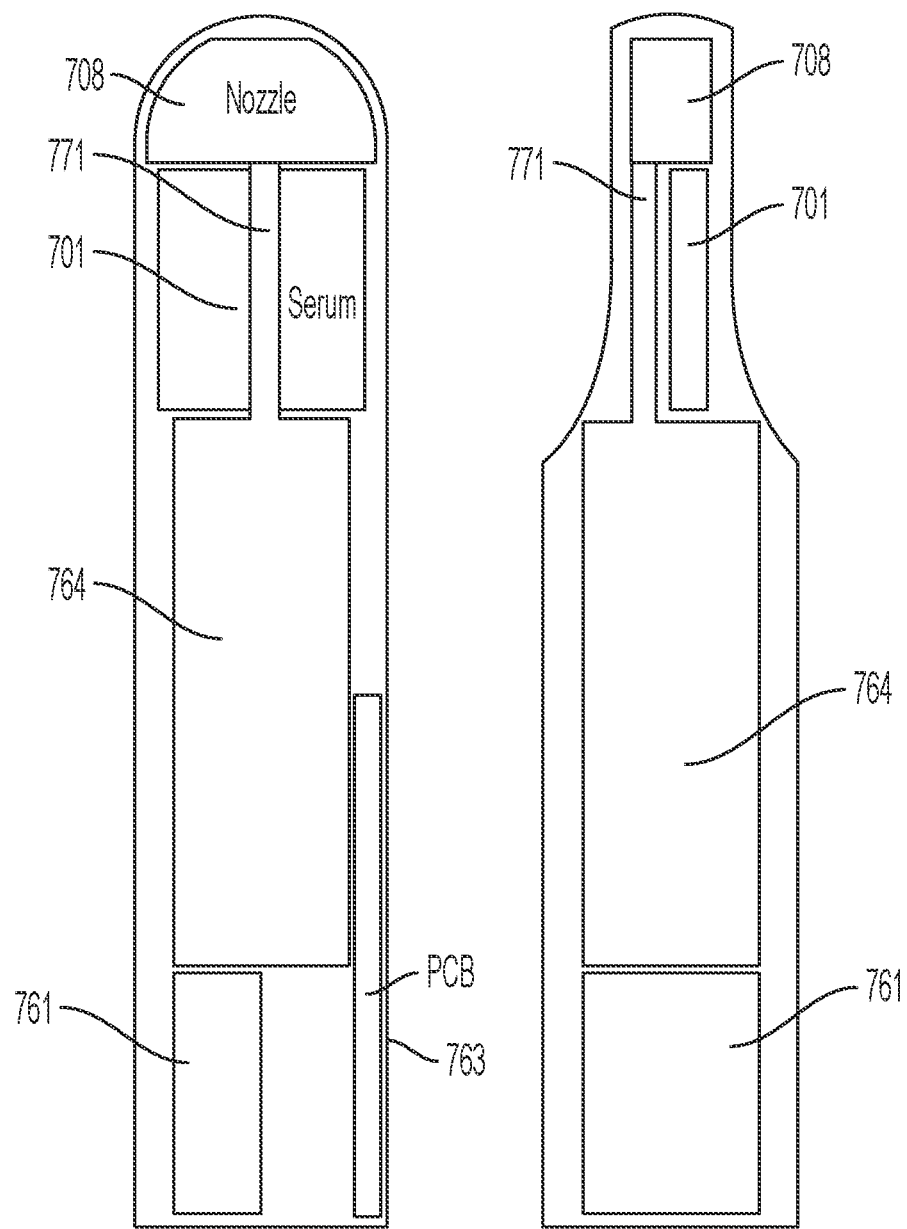
FIG. 7A shows a schematic view of a dermal spray device according to an aspect of the invention.
Figure 7B:
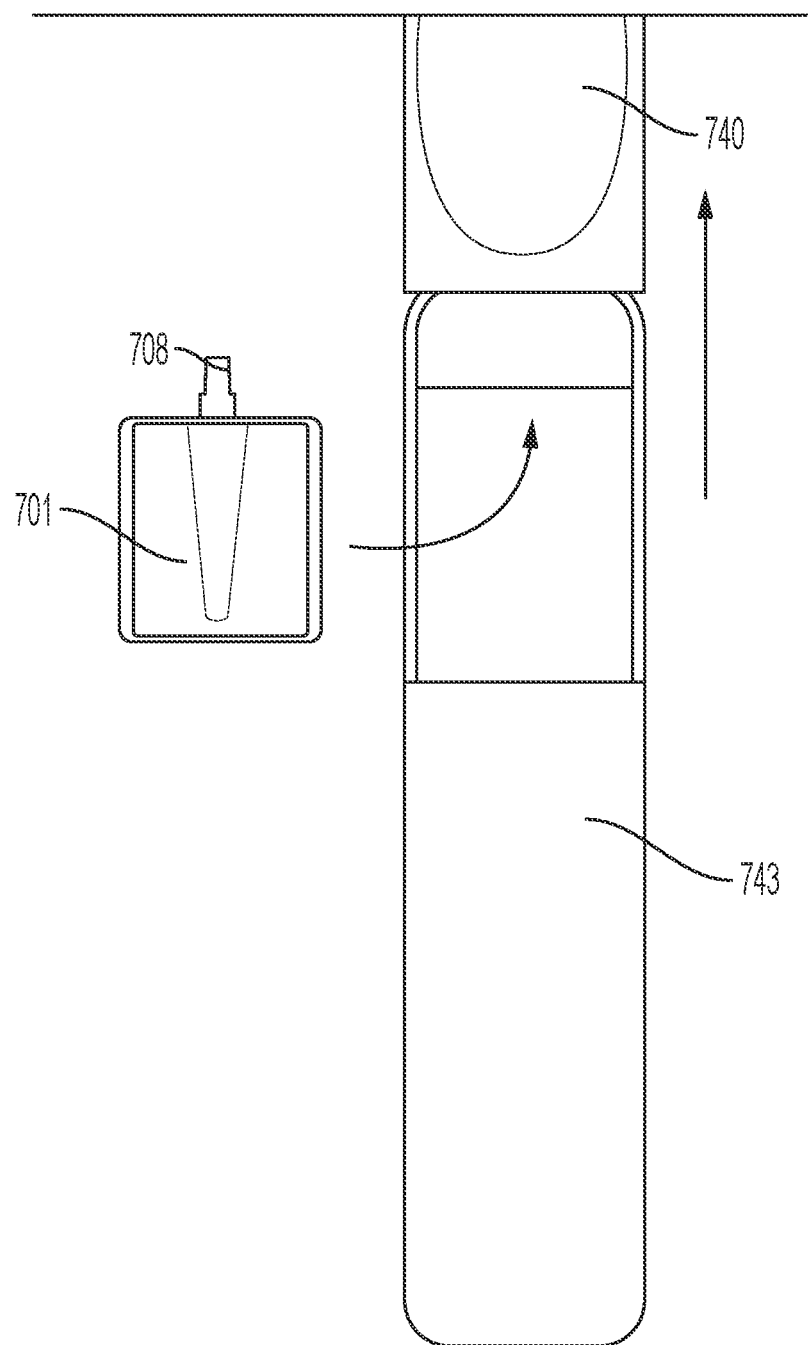
FIG. 7B shows a perspective view of the dermal spray device shown schematically in FIG. 7A.

FIG. 7A-B show another dermal spray device where a cartridge is inserted and positioned into place by a vertically sliding door 743. The device includes a nozzle body 708 connected to a reservoir 701, a compressor 764 and a fluid conduit 771 connecting the compressor 764 to the nozzle body 708. The device includes a printed circuit board 763 and a battery 761. A perspective view of the dermal spray device is shown in FIG. 7B showing the motion of the door 743 that encloses the cartridge within the handle body 740 of the dermal spray device.

Figure 8A:
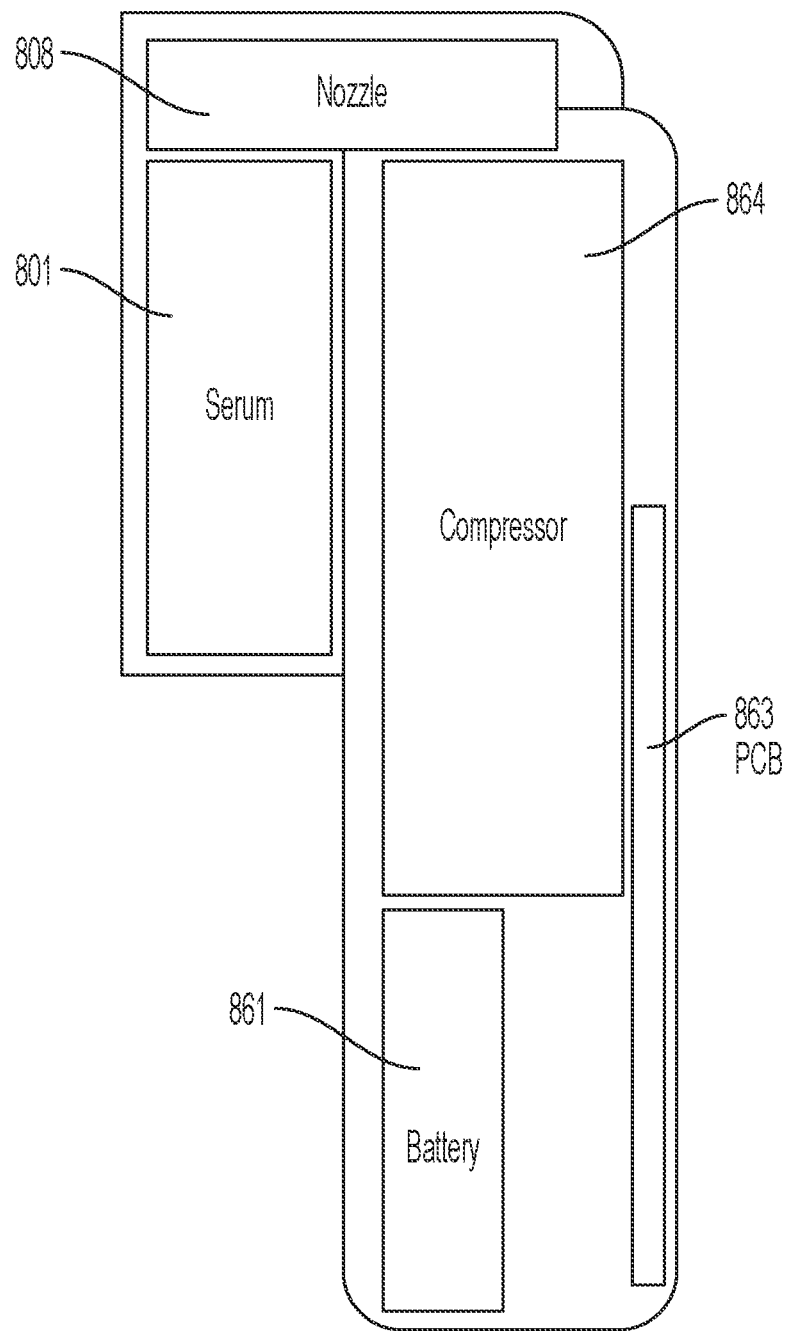
FIG. 8A shows a schematic view of a dermal spray device according to an aspect of the invention.
Figure 8B:
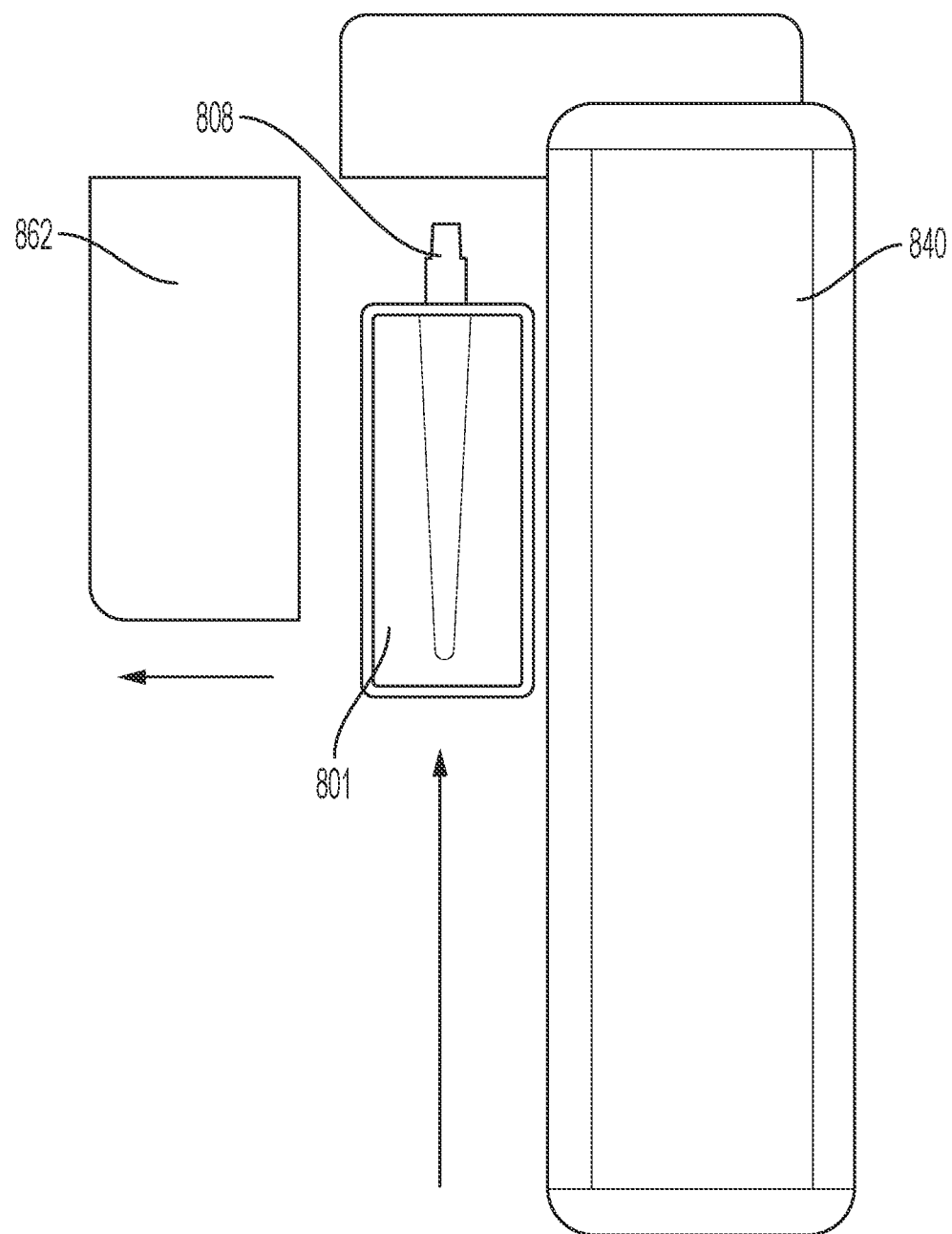
FIG. 8B shows a perspective view of the dermal spray device shown schematically in FIG. 8A.

FIG. 8A-B show a dermal spray device where a cartridge is inserted and positioned by pushing up into a receiver and then enclosed with a cartridge tray 862. The device includes a nozzle body 808 connected to a reservoir 801, and a compressor 864. The device includes a printed circuit board 863 and a battery 861. A side view of the dermal spray device is shown in FIG. 8B showing the motion of the cartridge tray 862 that encloses the cartridge within the handle body 840 of the dermal spray device.

Figure 9A:
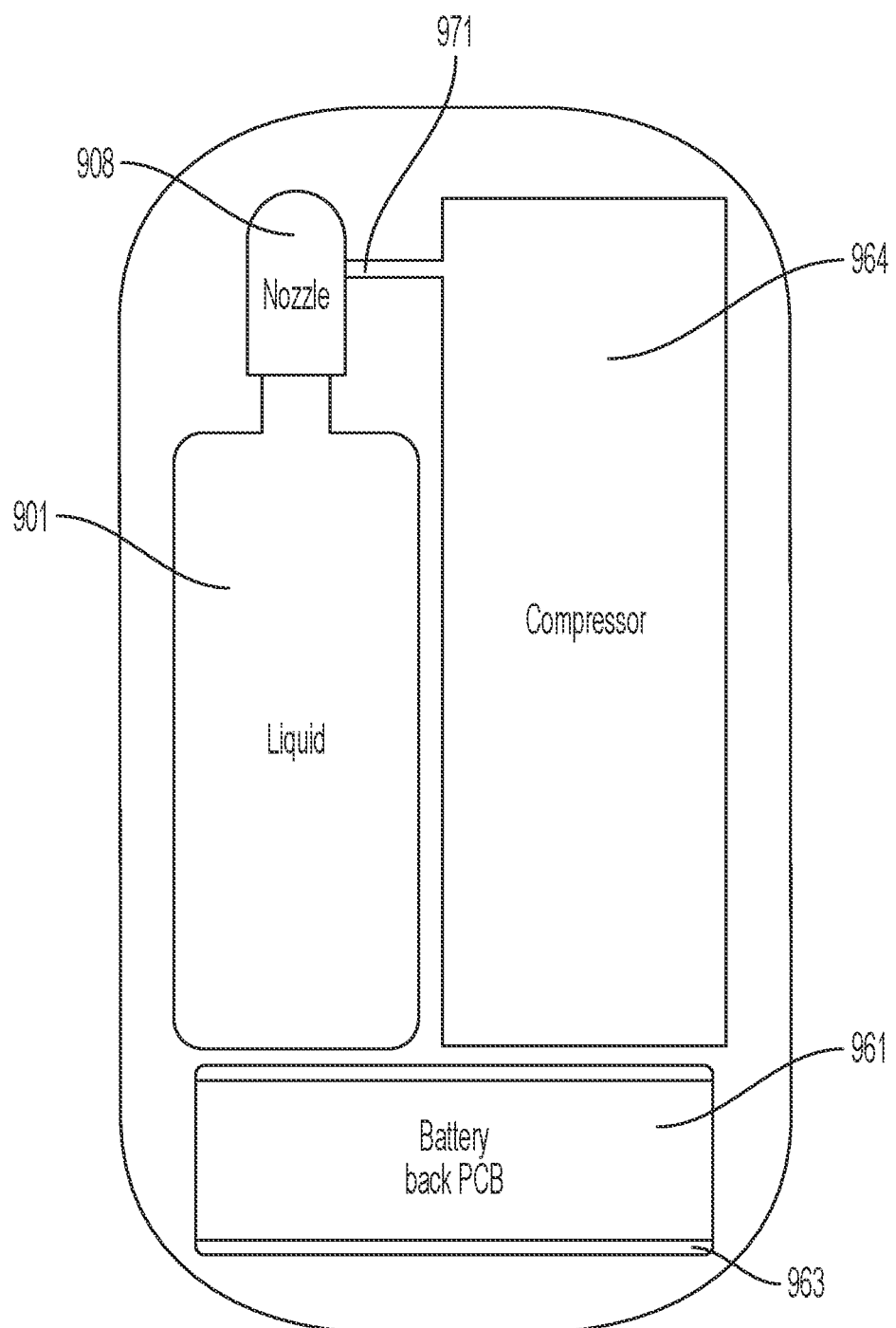
FIG. 9A shows a schematic view of a dermal spray device according to an aspect of the invention.
Figure 9B:
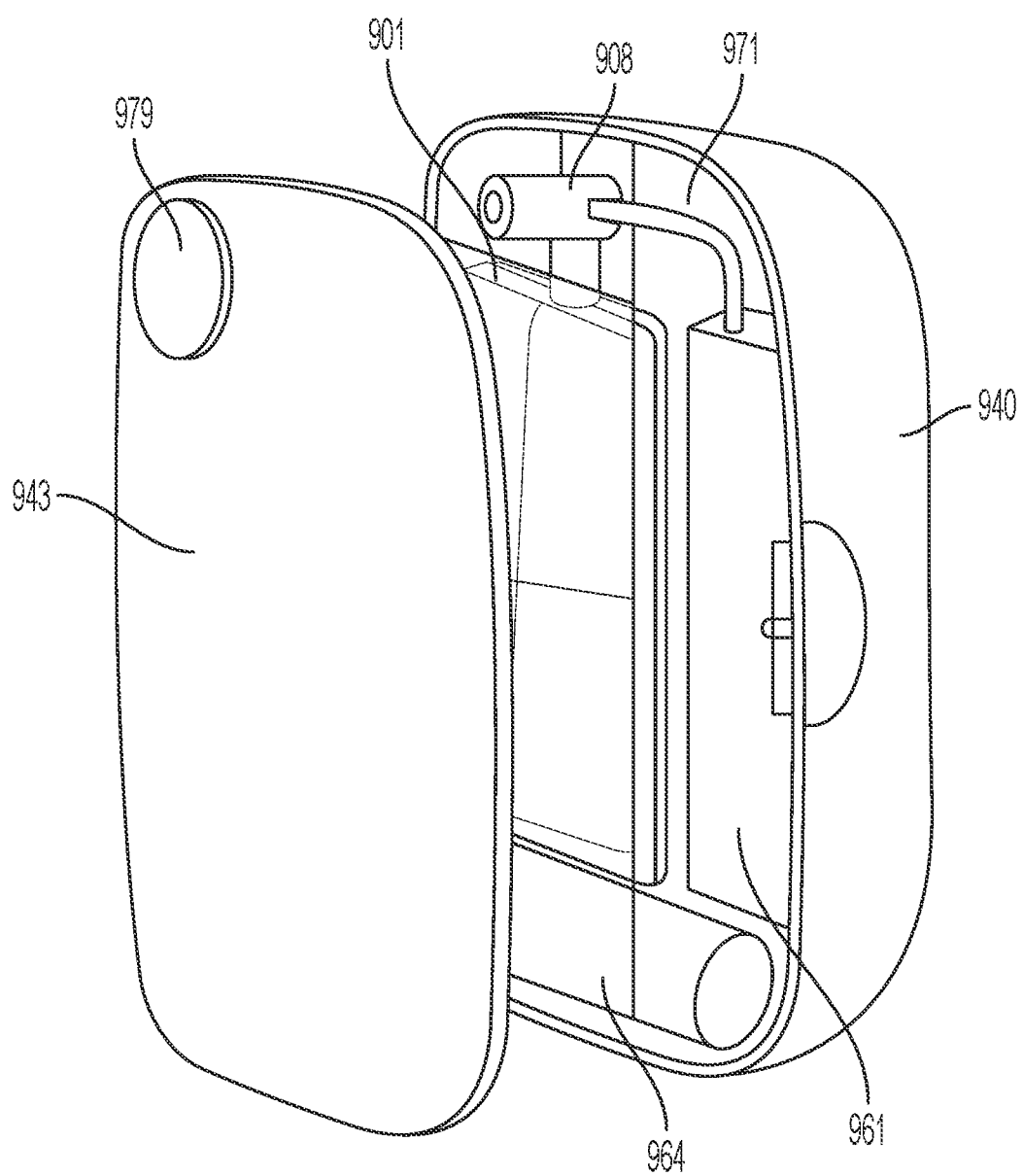
FIG. 9B shows a perspective view of the dermal spray device shown schematically in FIG. 9A.

FIG. 9A-B show a dermal spray device where a cartridge is inserted and positioned laterally into the device and closed by a door 943. The device includes a nozzle body 908 connected to a reservoir 901, a compressor 964 and a fluid conduit 971 connecting the compressor 964 to the nozzle body 908. The device includes a printed circuit board 963 and a battery 961. A perspective view of the dermal spray device is shown in FIG. 9B showing the motion of the door 943 that encloses the cartridge within the handle body 940 of the dermal spray device. The door 943 includes an spray opening 979 that allows spray from the nozzle to pass through.

Figure 10A:
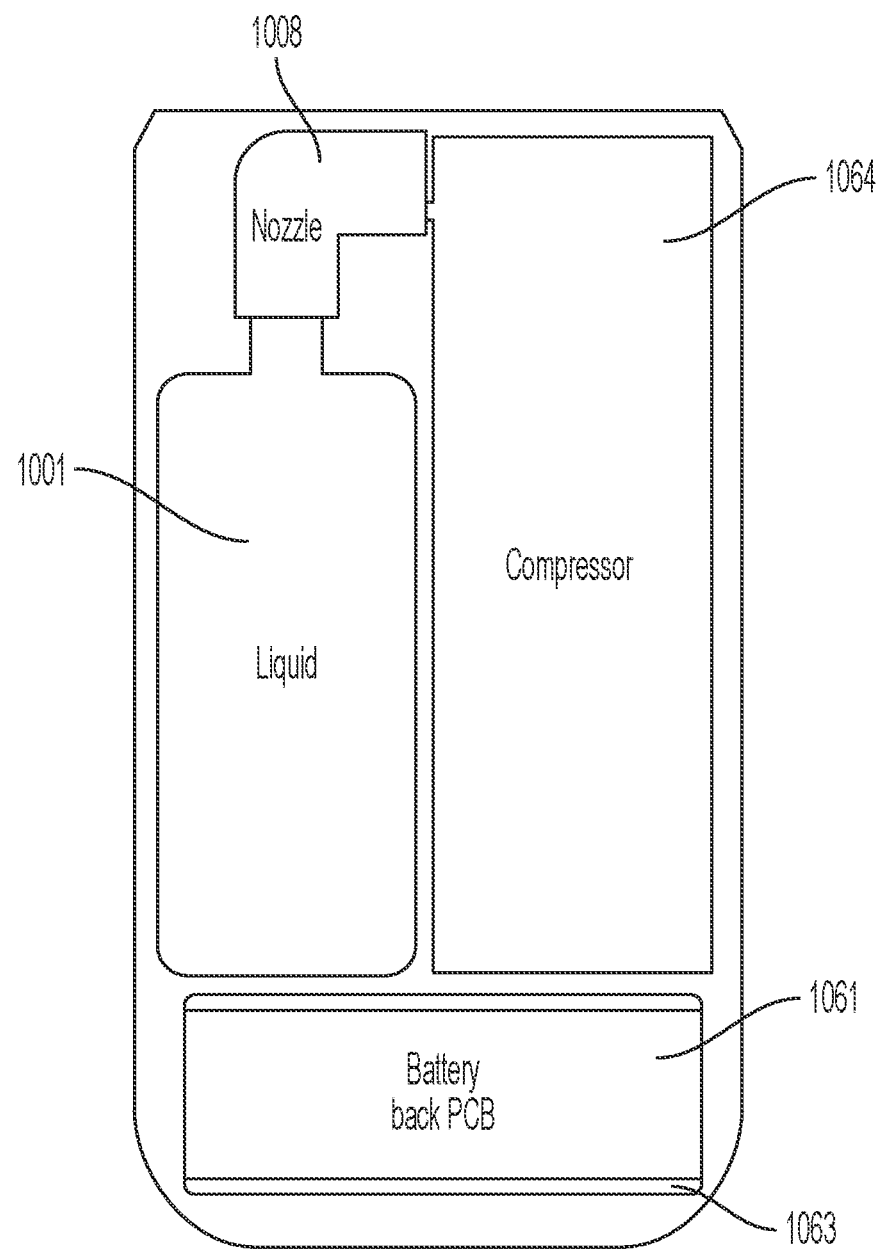
FIG. 10A shows a schematic view of a dermal spray device according to an aspect of the invention.
Figure 10B:
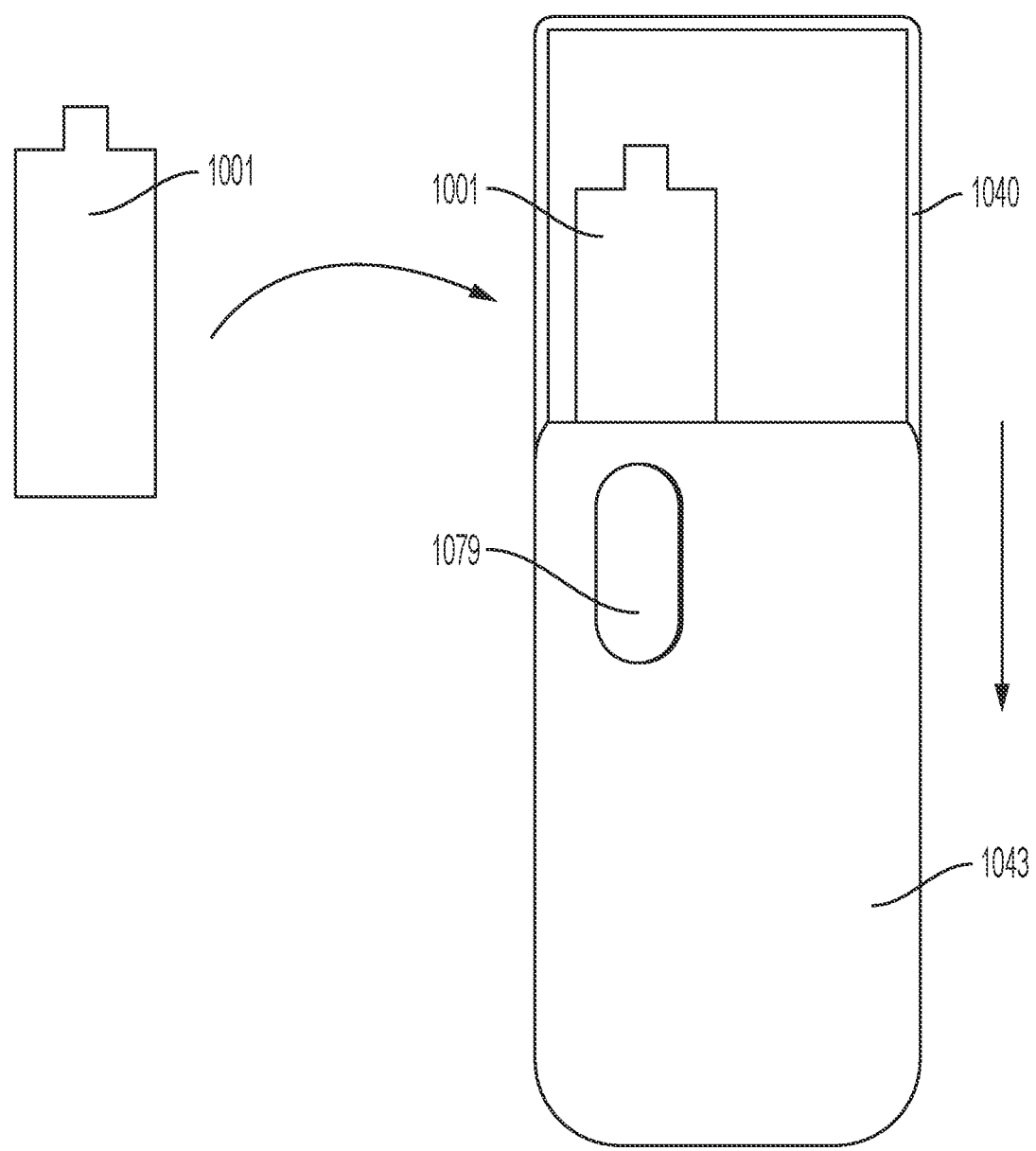
FIG. 10B shows a perspective view of the dermal spray device shown schematically in FIG. 10A.

FIG. 10A-B show a dermal spray device where a cartridge is inserted and positioned laterally into the device and closed by a vertically sliding door 1043. The device includes a nozzle body 1008 connected to a reservoir 1001, a compressor 1064 and a fluid conduit connecting the compressor 1064 to the nozzle body 1008. The device includes a printed circuit board 1063 and a battery 1061. A side view of the dermal spray device is shown in FIG. 10B showing the motion of the door 1043 that encloses the cartridge within the handle body 1040 of the dermal spray device. The door 1043 includes an spray opening 1079 that allows spray from the nozzle to pass through.

Other embodiments and uses of the invention will be apparent to those skilled in the art from consideration of the specification and practice of the invention disclosed herein. All references cited herein, including all U.S. and foreign patents and patent applications, are specifically and entirely hereby incorporated herein by reference. It is intended that the specification and examples be considered exemplary only, with the true scope and spirit of the invention indicated by the following claims.

What is claimed is:

1. A cartridge for spraying a liquid comprising:
a nozzle assembly, a liquid reservoir, and a cap attached to the liquid reservoir comprising at least one guide structure, wherein the cap is adapted to engage the nozzle assembly and allow for movement of the nozzle assembly in a controlled direction relative to the cap and the liquid reservoir, the controlled direction being defined by the at least one guide structure;
the nozzle assembly comprising a nozzle body, the nozzle body having an inner body and an outer body, the inner body being coaxial with the outer body, the inner body and outer body forming a first fluid passage therebetween, the first fluid passage adapted to deliver compressed air, the inner body comprising a second fluid passage in its interior, the second fluid passage adapted to deliver liquid from the liquid reservoir;
wherein the nozzle assembly is attached to the cap and the nozzle body, including the inner body and outer body, remains moveable in the controlled direction relative to the cap and the liquid reservoir while attached to the cap;
wherein the nozzle assembly is configured such that the liquid reservoir is initially sealed and when the nozzle assembly is moved in the controlled direction relative to the cap and the liquid reservoir, the movement of the inner body of the nozzle assembly relative to the cap pierces the sealed liquid reservoir to allow liquid from the liquid reservoir to flow into the second fluid passage of the nozzle assembly.

2. The cartridge of claim 1, wherein the nozzle assembly comprises a guide on an outer surface of the nozzle assembly that is adapted to translate lateral motion into vertical motion for engaging the nozzle assembly with the liquid reservoir.

3. The cartridge of claim 1, wherein the fluid reservoir comprises a pouch and the cap seals the pouch.

4. The cartridge of claim 1, wherein the cap includes recesses for capturing air bubbles in the fluid of the reservoir.

5. The cartridge of claim 1, wherein the at least one guide structure is configured to guide a flange on the inner body of the nozzle assembly.

6. The cartridge of claim 5, wherein the guide flange is designed to guide movement of the nozzle assembly in a rotational direction relative to the liquid reservoir in addition to a back and forth direction relative to the liquid reservoir.

7. The cartridge of claim 1, wherein the nozzle body has a conical shape.

8. The cartridge of claim 1, wherein the nozzle body has a rectangular shape.

9. The cartridge of claim 1, wherein the nozzle body has a rectangular shape and the first fluid path and second fluid path exit the nozzle body at about a 45 degree angle relative to the horizontal.

10. The cartridge of claim 1, wherein the nozzle body comprises a first guide member and a second guide member, wherein the first guide member and second guide member are adapted to engage with the cap in a manner that permits the nozzle assembly to move in a controlled direction relative to the cap.

11. The cartridge of claim 1, wherein the at least one guide structure comprises a guide post that is adapted to receive the nozzle assembly.

12. The cartridge of claim 11, wherein the guide post includes at least one guide slot, the at least one guide slot being adapted to engage a guide flange on the outside of the inner body of the nozzle assembly.

13. The cartridge of claim 12, wherein the guide slot is straight and provides for only back and forth movement of the nozzle assembly relative to the reservoir.

14. The cartridge of claim 12, wherein the guide slot is curved and thereby provides rotation as well as back and forth movement of the nozzle assembly relative to the reservoir.

* * * * *